US010260113B2

(12) United States Patent
Chen et al.

(10) Patent No.: US 10,260,113 B2
(45) Date of Patent: Apr. 16, 2019

(54) MULTIPLEX DETECTION ASSAY FOR INFLUENZA AND RSV VIRUSES

(71) Applicant: Quest Diagnostics Investments Incorporated, Wilmington, DE (US)

(72) Inventors: Jules Chen, Walnut, CA (US); Lilly I. Kong, Covina, CA (US); Ming-Chou Lee, Mission Viejo, CA (US); Fan Chen, Fullerton, CA (US); Michelle M. Tabb, Santa Ana, CA (US); Michael Aye, Fountain Valley, CA (US)

(73) Assignee: QUEST DIAGNOSTICS INVESTMENTS INCORPORATED, Wilmington, DE (US)

( * ) Notice: Subject to any disclaimer, the term of this patent is extended or adjusted under 35 U.S.C. 154(b) by 0 days.

(21) Appl. No.: 13/710,791

(22) Filed: Dec. 11, 2012

(65) Prior Publication Data
US 2014/0106990 A1    Apr. 17, 2014

Related U.S. Application Data

(62) Division of application No. 11/963,699, filed on Dec. 21, 2007, now Pat. No. 8,354,230.

(51) Int. Cl.
*C12N 15/00* (2006.01)
*C12Q 1/70* (2006.01)

(52) U.S. Cl.
CPC .................................. *C12Q 1/701* (2013.01)

(58) Field of Classification Search
CPC ........................................................ C12Q 1/68
See application file for complete search history.

(56) References Cited

U.S. PATENT DOCUMENTS

| | | | |
|---|---|---|---|
| 5,135,717 A | | 8/1992 | Renzoni et al. |
| 5,187,060 A | | 2/1993 | Cerutti et al. |
| 5,474,796 A | * | 12/1995 | Brennan .................. 427/2.13 |
| 5,652,099 A | | 7/1997 | Conrad |
| 5,846,717 A | | 12/1998 | Brow et al. |
| 6,001,567 A | | 12/1999 | Brow et al. |
| 6,015,664 A | | 1/2000 | Henrickson et al. |
| 6,268,132 B1 | | 7/2001 | Conrad |
| 6,811,971 B2 | | 11/2004 | Klepp et al. |
| 6,881,835 B2 | | 4/2005 | Bai et al. |
| 7,572,904 B2 | | 8/2009 | Cheng et al. |
| 2005/0202414 A1 | * | 9/2005 | Jia et al. ............. 435/5 |
| 2006/0210967 A1 | * | 9/2006 | Agan et al. ............. 435/5 |
| 2006/0257860 A1 | * | 11/2006 | Marlowe et al. .......... 435/5 |
| 2008/0003565 A1 | * | 1/2008 | Baptista et al. .......... 435/5 |
| 2009/0305229 A1 | * | 12/2009 | McBride et al. .......... 435/5 |

FOREIGN PATENT DOCUMENTS

| | | |
|---|---|---|
| CN | 1544656 | 11/2004 |
| WO | WO 9421797 A1 * | 9/1994 |
| WO | WO 2000/017391 | 3/2000 |
| WO | WO 2005/012572 | 2/2005 |

OTHER PUBLICATIONS

Wang et al. (Identifying Influenza Viruses with Resequencing Microarrays, Emerging Infectious Diseases, vol. 12, No. 4, Apr. 2006).*
Nolan et al. (Quantification of mRNA using real-time RT-PCR, Nature Protocols, vol. 1, No. 3, Nov. 9, 2006).*
Zhang et al. (Detection and identification of human influenza viruses by the polymerase chain reaction, Journal of Virological Methods, 33 (1991) 165-189).*
NCBI Accession No. M91479 (May 30, 2006).*
NCBI Accession No. AY58973 (Dec. 6, 2004).*
Rozen et al. (Primer3 on the WWW for General Users and for Biologist Programmers, in Methods in Molecular Biology, vol. 132: Bioinformatics Methods and Protocols, 2000).*
Solinas et al. (Duplex Scorpion primers in SNP analysis and FRET applications, Nucleic Acids Research, 2001, vol. 29. No. 20).*
Whitcombe (Scorpions Technology for Real Time PCR and Genotyping, attached, Mar. 1, 2003).*
Buck ("Design Strategies and Performance of Custom DNA Sequencing Primers" Biotechniques. 1999. 27(3): pp. 528-536).*
Lowe (Nucleic Acids Research, vol. 18, No. 7, p. 1757-1761, 1990).*
Lo (Introduction to the Polymerase Chain Reaction, in Methods in Molecular Medicine, vol. 16, Chemical Applications of PCR, 1998).*
SantaLucia (Physical Principles and Visual-OMP Software for Optimal PCR Design, in PCR Primer Design, Methods in Molecular Biology, 2007).*
NCBI Accession No. CY018398 (Dec. 29, 2006).*
Premier Biosoft (Scorpion primers or probes for real time PCR, attached, Jul. 29, 2007).*
Schoske (Multiplex PCR design strategy used for the simultaneous amplification of 10 Y chromosome short tandem repeat (STR) loci, Anal Bioanal Chem. Feb. 2003;375(3):333-43. Epub Jan. 14, 2003).*
Coleman et al. (Simultaneous Quantification of Four RNA Targets by Multiplex, Real-Time RT-PCR without Optimization, Biotechniques. Sep. 2007;43(3):369-71).*
Edwards et al. (Multiplex PCR: Advantages, Development, and Applications, PCR Methods Appl. Feb. 1994;3(4):S65-75).*
Henegariu et al. (Multiplex PCR: Critical Parameters and Step-by-Step Protocol, Biotechniques. Sep. 1997;23(3):504-11).*
Boivin et al. (Multiplex Real-Time PCR Assay for Detection of Influenza and Human Respiratory Syncytial Viruses, J. Clin. Microbiol. Jan. 2004 vol. 42 No. 1 45-51).*
Mentel et al. (Real-time PCR to improve the diagnosis of respiratory syncytial virus infection, J Med Microbiol. Oct. 2003;52(Pt 10):893-6).*

(Continued)

*Primary Examiner* — Aaron A Priest
(74) *Attorney, Agent, or Firm* — Foley & Lardner LLP

(57) ABSTRACT

The present invention generally relates to a molecular test of Influenza A, Influenza B, Respiratory Syncytial Virus A, and Respiratory Syncytial Virus B in order to identify patients with a viral infection. Accordingly methods and compositions are disclosed to determine the presence or absence of a viral pathogen in a sample containing one or more target nucleic acids from the M gene of Influenza A, Influenza B, Respiratory Syncytial Virus A, and/or Respiratory Syncytial Virus B.

4 Claims, 12 Drawing Sheets

Specification includes a Sequence Listing.

(56) References Cited

OTHER PUBLICATIONS

Osiowy et al. (Direct Detection of Respiratory Syncytial Virus, Parainfluenza Virus, and Adenovirus in Clinical Respiratory Specimens by a Multiplex Reverse Transcription-PCR Assay, J Clin Microbiol. Nov. 1998;36(11):3149-54).*

Stockton et al. (Multiplex PCR for Typing and Subtyping Influenza and Respiratory Syncytial Viruses, J Clin Microbiol. Oct. 1998;36(10):2990-5).*

Templeton et al. (Rapid and Sensitive Method Using Multiplex Real-Time PCR for Diagnosis of Infections by Influenza A and Influenza B Viruses, Respiratory Syncytial Virus, and Parainfluenza Viruses 1, 2, 3, and 4, J Clin Microbiol. Apr. 2004;42(4):1564-9).*

Lam et al. (Rapid Multiplex Nested PCR for Detection of Respiratory Viruses, J Clin Microbiol. Nov. 2007; 45(11): 3631-3640).*

Li et al. (Typing and subtyping influenza virus using DNA microarrays and multiplex reverse transcriptase PCR, J Clin Microbiol. Feb. 2001;39(2):696-704).*

Fouchier et al. (Detection of influenza A viruses from different species by PCR amplification of conserved sequences in the matrix gene, J Clin Microbiol. Nov. 2000;38(11):4096-101).*

Machado et al. (Use of Oseltamivir to control influenza complications after bone marrow transplantation, Bone Marrow Transplant. Jul. 2004;34(2):111-4).*

Peck et al. (Respiratory virus infection among hematopoietic cell transplant recipients: evidence for asymptomatic parainfluenza virus infection, Blood. Sep. 1, 2007;110(5):1681-8. Epub May 14, 2007).*

Bhat et al. (Influenza-associated deaths among children in the United States, 2003-2004, N Engl J Med. Dec. 15, 2005;353(24):2559-67).*

Kuypers et al. (Evaluation of quantitative and type-specific real-time RT-PCR assays for detection of respiratory syncytial virus in respiratory specimens from children, J Clin Virol. Oct. 2004;31(2):123-9).*

Stratagene (Gene Characterization Kits; 1988).*

Weiner et al. (Kits and their unique role in molecular biology: a brief retrospective, BioTechniques 44:701-704 (25th Anniversary Issue, Apr. 2008)).*

Bellau-Pujol, S. et al., Development of three multiplex RT-PCR assays for the detection of 12 respiratory RNA viruses., J. Virol Methods, Jun;126(1-2):53-63 (2005).

Boivin, G. et al., Multiplex Real-Time PCR Assay for Detection of Influenza and Human Respiratory Syncytial Viruses, J. Clin. Microbiol. Jan; 42(1):45-51 (2004).

Cheng, S.M. et al., Detection of influenza B in clinical specimens: comparison of high throughput RT-PCR and culture confirmation, Virus Res., Jul;103(1-2):85-90 (2004).

Coiras, M.T. et al., Simultaneous Detection of Influenza A, B, and C Viruses, Respiratory Syncytial Virus, and Adenoviruses in Clinical Samples by Multiplex Reverse Transcription Nested-PCR Assay, J Med Virol. Jan;69(I):132-44. (2003).

Coiras, M.T. et al., Oligonucleotide Array for Simultaneous Detection of Respiratory Viruses Using a Reverse-Line Blot Hybridization Assay, J. Med. Virol. Jun;76(2):256-64. (2005).

Ellis, J.S., Fleming, D.M., and Zambon, M.C., Multiplex Reverse Transcription-PCR for Surveillance of Influenza A and B Viruses in England and Wales in 1995 and 1996, J. Clin. Microbiol., Aug;35(8):2076-82 (1997).

Fan, J., Henrickson, K.J., and Savatski, L.L., Rapid Simultaneous Diagnosis of Infections with Respiratory Syncytial Viruses A and B, Influenza Viruses A and B, and Human Parainfluenza Virus Types 1, 2, and 3 by Multiplex Quantitative Reverse Transcription-Polymerase Chain Reaction-Enzyme Hybridization Assay (Hexaplex), Clin. Infect. Dis., Jun. 26(6)1397-402 (1998).

Grondahl, B. et al., Rapid Identification of Nine Microorganisms Causing Acute Respiratory Tract Infections by Single-Tube Multiplex Reverse Transcription-PCR: Feasibility Study, J. Clin. Microbiol., Jan;37(1):1-7 (1999).

Hafner, et al., Isothermal Amplification and Multimerization of DNA by Bst DNA Polymerase, Biotechniques Apr;30(4):852-6, 858, 860 (2001).

Heid, et al., Real time quantitative PCR, *Genome Res* 6:986-994 (1996).

Jameson, D.M., Eccleston, J.M., Fluorescent Nucleotide Analogs: Synthesis and Applications, *Meth. Enzymol.* 278:363-390 (1997).

Li, J., Chen, S. and Evans, D. H., Typing and Subtyping Influenza Virus Using DNA Microarrays and Multiplex Reverse Transcriptase PCR, J. Clin. Microbial., Feb;39(2):696-704 (2001).

Lin , Y.P. et al., Recent changes among human influenza viruses., Virus Res., Jul;103(1-2):47-52. Review. (2004).

Liolios, L. et al., Comparison of a Multiplex Reverse Transcription-PCR-Enzyme Hybridization Assay with Conventional Viral Culture and Immunofluorescence Techniques for the Detection of Seven Viral Respiratory Pathogens, J. Clin. Microbiol., Aug;39(8):2779-83 (2001).

Lyamichev, V. et al., Polymorphism identification and quantitative detection of genomic DNA by invasive cleavage of oligonucleotide probes, *Nature Biotechnology*, 17:292-296 (1999).

Mansfield et al., Nucleic acid detection using non-radioactive labeling methods, *Mol. Cell.* Probes 145-156 (1995).

Meerhoff, T.J. et al., Harmonising the virological surveillance of influenza in Europe: results of an 18-country survey, Virus Res., Jul;103(1-2):31-3. (2004).

Payungporn, S. et al., Single step multiplex real-time RT-PCR for H5N1 influenza virus detection, J. Virol. Methods, Feb;131(2):143-7. Epub Sep. 23, 2005.

Pechirra, P. et al., Molecular Characterization of the HA Gene of Influenza Type B Viruses, J. Med. Virol. Dec;77(4):541-9. (2005).

Puppe, W. et al., Evaluation of a multiplex reverse transcriptase PCR ELISA for the detection of nine respiratory tract pathogens, J. Clin. Virol. Jun;30(2):165-74 (2004).

Ryan, D., Nuccie, B., and Arvan, D., Non-PCR-Dependent Detection of the Factor V Leiden Mutation From Genomic DNA Using a Homogeneous Invader Microtiter Plate Assay, *Molecular Diagnosis* 4(2):135-144 (1999).

Saiki, R.K., "Amplification of Genomic DNA" in *PCR Protocols*, Innis et al., Eds., Academic Press, San Diego, CA pp. 13-20 (1990).

Stockton, J. et al., Multiplex PCR for Typing and Subtyping Influenza and Respiratory Syncytial Viruses, J. Clin. Microbiol., Oct;36(10):2990-5 (1998).

Sullender, W.M., Respiratory Syncytial Virus Genetic and Antigenic Diversity. Clin. Microbiol. Rev. Jan;13(1):1-15, table of contents. Review. (2000).

Templeton, K.E. et al., Rapid and Sensitive Method Using Multiplex Real-time PCR for Diagnosis of Infections by Influenza A and Influenza B Viruses, Respiratory Syncytial Virus, and Parainfluenza Viruses 1, 2, 3, and 4., J. Clin. Microbiol., 42(4):1564-1569 (2004).

Thompson, W.W. et al., Mortality Associated with Influenza and Respiratory Syncytial Virus in the United States. JAMA. Jan. 8:289(2):179-86 (2003).

Tyagi, S., Bratu, D.P., and Kramer, F.R., Multicolor molecular beacons for allele discrimination, Nature Biotechnology 16:49-53 (1998).

Ushio, M. et al., Detection of Respiratory Syncytial Virus Genome by Subgroups-A, B Specific Reverse Transcription Loop-Mediated Isothermal Amplification (RT-LAMP). J. Med. Virol., Sep;77(1):121-7 (2005).

Valassina, M. et al., Rapid detection of different RNA respiratory virus species by multiplex RT-PCR: application to clinical specimens. Clin. Diagn. Virol., Nov;8(3):227-32 (1997).

Van Elden, L.J., et al., Simultaneous Detection of Influenza Viruses A and B Using Real-Time Quantitative PCR. J. Clin. Microbiol., Jan;39(1):196-200 (2001).

Wallace, L.a. et al., Virological surveillance of influenza-like illness in the community using PCR and serology., J. Clin. Virol., Sep;31(1):40-5. (2004).

Wharam, et al., Specific detection of DNA and RNA targets using a novel isothermal nucleic acid amplification assay based on the formation of a three-way junction structure, Nucleic Acids Res. Jun. 1;29(11):E54-E54 (2001).

Whitcombe et al., Detection of PCR products using self-probing amplicons and flurescence, Nature Biotech. 17: 804-807 (1999).

Xu, X. et al., Reassortment and evolution of current human influenza A and B viruses, Virus Res., Jul;103(1-20:55-60. (2004).

(56) References Cited

OTHER PUBLICATIONS

Zambon, M.C. et al., Contribution of influenza and respiratory syncytial virus to community cases of influenza-like illness: an observational study. Lancet, Oct. 27;358(9291):1410-6. (2001).
Zhu, Z. et al., Directly labeled DNA probes using fluorescent nucleotides with different length linkers, 22 *Nucl. Acids Res.* 3418-3422 (1994).
Satake et al., "Nucleotide Sequence of the Gene Encoding Respiratory Syncytial Virus Matrix Protein," vol. 50, No. 1, pp. 92-99, 1984.
Lowe et al., "A computer program for selction of oligonucleotide primers for polymerase chain reactions," Nucleic Acid Research, vol. 18, No. 7, pp. 1757-1761, 1990.
McCuller et al., "Multiple Genotypes of Influenza B Virus Circulated between 1979 and 2003," J. of Virology, vol. 78, No. 23, pp. 12817-12828, 2004.
The nucleic acid search reports for SEQ ID No. 13-14, 16-18, 21-22, 25-26, 32-35.
International Search Report dated Jun. 5, 2009 in application No. PCT/US08/86936.
Kuypers et al., "Evaluation of quantitative and type-specific real-time RT-PCR assays for detection of respiratory syncytial virus in respiratory specimens from children," J. Clin. Virol., vol. 31, No. 2, pp. 123-129, Oct. 2004.
Office Action dated Sep. 2, 2010 in U.S. Appl. No. 11/963,699.
Office Action dated Nov. 29, 2010 in U.S. Appl. No. 11/963,699.
Office Action dated May 11, 2011 in U.S. Appl. No. 11/963,699.
Office Action dated Oct. 26, 2011 in U.S. Appl. No. 11/963,699.
Office Action dated Apr. 10, 2012 in U.S. Appl. No. 11/963,699.
Notice of Allowance dated Sep. 14, 2012 in U.S. Appl. No. 11/963,699.

\* cited by examiner

FIGURE 1. *Influenza A* Virus, Matrix Protein 1 and Matrix Protein 2 Genes (M gene), Segment 7; GenBank Accession No. CY002353 (SEQ ID NO: 1)

```
   1 agcaaaagca ggtagatatt gaaagatgag ccttctaacc gaggtcgaaa cgtatgttct
  61 ctctatcgtt ccatcaggcc ccctcaaagc cgaaatcgcg cagagacttg aagatgtctt
 121 tgctgggaaa aacacagatc ttgaggctct catggaatgg ctaaagacaa gaccaattct
 181 gtcacctctg actaagggga ttttggggtt tgtgttcacg ctcaccgtgc ccagtgagcg
 241 aggactgcag cgtagacgct ttgtccaaaa tgcccttaat gggaatgggg atccaaataa
 301 catggacaaa gcagtcaaac tgtatagaaa acttaagagg gagataacat tccatggggc
 361 caaagaaata gcactcagtt attctgctgg tgcacttgct agttgcatgg gcctcatata
 421 caataggatg gggctgtaa ccaccgaagt ggcatttggc ctggtatgtg caacatgtga
 481 acagattgct gactcccagc acaggtctca taggcaaatg gtggcaacaa ccaatccatt
 541 aataaaacat gagaacagaa tggtttggc cagcactaca gctaaagcta tggagcaaat
 601 ggctggatca agtgagcagg cagcggaggc catggagatt gctagtcagg ccaggcaaat
 661 ggtgcaggca atgagaaccg ttgggactca tcctagttcc agtactggtc taagagatga
 721 tcttcttgaa aatttgcaga cctatcagaa acgaatggga gtacagatgc agcgattcaa
 781 gtgacccgct tgttgttgct gcgagtatca ttgggatctt gcacttgata ttgtggattc
 841 ttgatcgtct tttttcaaa tgcatctatc gactcttcaa acacggcctg aaaagagggc
 901 cttctacgga aggagtacct gagtctatga gggaagaata tcggaaggaa cagcagaatg
 961 ctgtggatgc tgacgacagt catttgtca gcatagagct ggagtaaaaa actaccttgt
1021 ttctact
```

FIGURE 2. *Influenza A* Virus, Matrix Protein 1 and Matrix Protein 2 Genes (M gene), Segment 7; GenBank Accession No. CY002985 (SEQ ID NO: 2)

```
   1 agcaaaagca ggtagatatt gaaagatgag tcttctaacc gaggtcgaaa cgtacgttct
  61 ctctatcgtc ccgtcaggcc ccctcaaagc cgagatcgca cagagacttg aagatgtatt
 121 tgctggaaag aataccgatc ttgaggctct catggagtgg ctaaagacaa gaccaatcct
 181 gtcacctctg actaagggga ttttaggatt tgtgttcacg ctcaccgtgc ccagtgagcg
 241 aggactgcaa cgtagacgct ttgtccaaaa tgcccttaat gggaatgggg atccaaataa
 301 tatggacaga gcagtcaaac tgtatcgaaa gcttaagagg gagataacat tccatggggc
 361 caaagaaata gcactcagtt attctgctgg tgcacttgcc agttgtatgg gactcatata
 421 caacaggatg ggggctgtga ccaccgaatc agcatttggc cttatatgcg caacctgtga
 481 acagattgcc gactcccagc ataagtctca taggcaaatg gtaacaacaa ccaatccatt
 541 aataagacat gagaacagaa tggttctggc cagcactaca gctaaggcta tggagcaaat
 601 ggctggatcg agtgaacaag cagctgaggc catggaggtt gctagtcagg ccaggcagat
 661 ggtgcaggca atgagagcca ttgggactca tcctagctct agcactggtc tgaaaaatga
 721 tctccttgaa aatttgcagg cctatcagaa acgaatgggg gtgcagatgc aacgattcaa
 781 gtgatcctct tgttgttgcc gcaagtataa ttgggattgt gcacctgata ttgtggatta
 841 ttgatcgcct tttttccaaa agcatttatc gtatctttaa acacggttta aaaagagggc
 901 cttctacgga aggagtacca gagtctatga gggaagaata tcgggaggaa cagcagaatg
 961 ctgtggatgc tgacgatggt cattttgtca gcatagagct agagtaaaaa actaccttgt
1021 ttctact
```

FIGURE 3. *Influenza A* Virus, Matrix Protein 1 and Matrix Protein 2 Genes (M gene), Segment 7; GenBank Accession No. CY002057 (SEQ ID NO: 3)

```
   1 agcaaaagca ggtagatatt gaaagatgag ccttctaacc gaggtcgaaa cgtatgttct
  61 ctctatcgtt ccatcaggcc ccctcaaagc cgagatcgcg cagagacttg aggatgtctt
 121 tgctgggaaa aacacagatc ttgaggctct catggaatgg ctaaagacaa gaccaattct
 181 gtcacctctg actaagggga ttttgggggtt tgtgttcacg ctcaccgtgc ccagtgagcg
 241 aggactgcag cgtagacgct ttgtccaaaa tgccctcaat gggaatggag atccaaataa
 301 catggacaaa gcagttaaac tgtataggaa acttaagagg gagataacgt tccatggggc
 361 caaagaaata gctctcagtt attctgctgg tgcacttgcc agttgcatgg gcctcatata
 421 caatagaatg ggggctgtaa ccactgaagt ggcatttggc ctggtatgtg caacatgtga
 481 acagattgct gactcccagc acaggtctca taggcaaatg gtggcaacaa ccaatccatt
 541 aataaaacat gagaacagaa tggtttttggc cagcactaca gctaaggcta tggagcaaat
 601 ggctgggtca agtgagcagg cagcggaggc catggaaatt gctagtcagg ccaggcgaat
 661 ggtgcaggca atgagagccg ttgggactca tcctagctcc agtactggtc taagagatga
 721 tcttcttgaa aatttgcaga cctatcagaa acgaatgggg gtgcagatgc aacgattcaa
 781 gtgacccgct tgttgttgcc gcgaatatca ttgggatctt gcacttgata ttgtggattc
 841 ttgatcgtct tttcttcaaa tgcgtctatc gactcttcaa acacggcctt aaaagaggcc
 901 cttctacgga aggagtacct gagtctatga gggaagaata tcgaaaggaa cagcagaatg
 961 ctgtggatgc tgacgacagt cattttgtca gcatagagtt ggagtaaaaa actaccttgt
1021 ttctact
```

FIGURE 4. *Influenza B* Virus, Matrix Protein 1 and BM2 Protein Genes (M gene); GenBank Accession No. AY581982 (SEQ ID NO: 4)

```
   1 atgtcgctgt tggagacac aattgcctac ctgctttcat tgacagaaga tggagaaggc
  61 aaagcagaac tagcagaaaa attacactgt tggtttggtg ggaaagaatt tgacttagac
 121 tctgccttgg aatggataaa aaacaaaaga tgcttaactg atatacaaaa agcactaatt
 181 ggtgcctcta tctgcttttt aaaacccaaa gaccaggaaa gaaaaagaag attcatcaca
 241 gagcccttat caggaatggg aacaacagca acaaaaaaga aaggcctgat tctggctgag
 301 agaaaaatga gaagatgtgt gagctttcat gaagcatttg aaatagcaga aggccatgaa
 361 agctcagcgc tactatactg tctcatggtc atgtacctga atcctggaaa ttattcaatg
 421 caagtaaaac taggaacgct ctgtgctttg tgcgagaaac aagcatcaca ttcacacagg
 481 gctcatagca gagcagcgag atcttcagtg cctggagtga gacgagaaat gcagatggtc
 541 tcagctatga acacagcaaa aacaatgaat ggaatgggaa aaggagaaga cgtccaaaag
 601 ctggcagaag agctgcaaag caacattgga gtgctgagat ctcttggggc aagtcaaaag
 661 aatggggaag gaattgcaaa ggatgtaatg gaagtgctaa agcagagctc tatgggaaat
 721 tcagctcttg tgaagaaata tctataatgc tcgaaccatt tcagattctt tcaatttgtt
 781 cttttatctt atcagctctc catttcatgg cttggacaat agggcatttg aatcaaataa
 841 aaagaggagt aaacatgaaa atacgaataa aaagtccaaa caaagagaca ataaacagag
 901 aggtatcaat tttgagacac agttaccaaa aagaaatcca ggccaaagaa acaatgaaga
 961 aagtactctc tgacaacatg gaggtattga gtgaccacat aataattgag gggctttctg
1021 ccgaagagat aataaaaatg ggtgaaacag ttttggagat agaagaattg cattaa
```

FIGURE 5. *Influenza B* Virus, Matrix Protein 1 and BM2 Protein Genes (M gene); GenBank Accession No. AY581981 (SEQ ID NO: 5)

```
   1 atgtcgctgt ttggagacac aattgcctac ctgctttcat tgacagaaga tggagaaggc
  61 aaagcagaac tagcagaaaa attacactgt tggttcggtg ggaaagaatt tgacctggac
 121 tctgccttgg aatggataaa aaacaaaaga tgcttaactg atatacaaaa agcactaatt
 181 ggtgcctcta tctgcttttt aaaacccaaa gaccaggaaa gaaaaagaag attcatcaca
 241 gagcctctat caggaatggg aacaacagca acaaaaaaga aaggtctgat tctagctgag
 301 agaaaaatga gaagatgtgt gagctttcat gaagcatttg aaatagcaga aggccatgaa
 361 agctcagcgc tactatactg tctcatggtc atgtacctga atcctggaaa ttattcaatg
 421 caagtaaaac taggaacgct ctgtgctttg tgcgagaaac aagcatcaca ttcacacagg
 481 gctcatagca gagcagcgag atcttcagtg cctggagtga gacgagaaat gcagatggtc
 541 tcagctatga acacagcaaa aacaatgaat ggaatgggaa aaggagaaga cgtccaaaaa
 601 ctggcagaag agctgcaaag caacattgga gtactgagat ctcttgggc aagtcaaaag
 661 aatggagaag gaattgcaaa ggatgtaatg gaagtgctaa agcagagctc tatgggaaat
 721 tcagctcttg tgaagaaata tctataatgc tcgaaccatt tcagattctt tcaatttgtt
 781 cttttatctt atcagctctc catttcatgg cttggacaat agggcatttg aatcaaataa
 841 aaagaggagt aaacatgaaa atacgaataa aaagtccaaa caaagagaca ataaacagag
 901 aggtatcaat tttgagacac agttaccaaa aagaaatcca ggccaaagaa acaatgaagg
 961 aggtactctc tgacaacatg gaggtattga gtgaccacat aataattgag gggctttctg
1021 ccgaagagat aataaaaatg ggtgaaacag ttttggagat agaagaattg cattaa
```

FIGURE 6. *Influenza B* Virus, Matrix Protein 1 and BM2 Protein Genes (M gene);
GenBank Accession No. AY581980 (SEQ ID NO: 6)

```
   1 atgtcgctgt tggagacac  aattgcctac ctgctttcat tgacagaaga tggagaaggc
  61 aaagcagaac tagcagaaaa attacactgt tggttcggtg ggaaagaatt tgacctagac
 121 tctgccttgg aatggataaa aaacaaaaga tgcttaactg atatacaaaa agcactaatt
 181 ggtgcctcta tctgcttttt aaaacccaaa gaccaggaaa gaaaaagaag attcatcaca
 241 gagcctctat caggaatggg aacaacagca acaaaaaaga aaggcctgat tctagctgag
 301 agaaaaatga gaagatgtgt gagctttcat gaagcatttg aaatagcaga aggccatgaa
 361 agctcagcgc tactatactg tctcatggtc atgtacctga atcctggaaa ttattcaatg
 421 caagtaaaac taggaacgct ctgtgctttg tgcgagaaac aagcatcaca ttcacacagg
 481 gctcatagca gagcagcgag atcttcagtg cctggagtga gacgagaaat gcagatggtc
 541 tcagctatga acacagcaaa aacaatgaat ggaatgggaa aaggagaaga cgtccaaaaa
 601 ctggcagaag agctgcaaag caacattgga gtactgagat ctcttggggc aagtcaaaag
 661 aatggagaag gaattgcaaa ggatgtaatg gaagtgctaa agcagagctc tatgggaaat
 721 tcagctcttg tgaagaaata tctataatgc tcgaaccatt tcagattctt tcaatttgtt
 781 cttttatctt atcagctctc catttcatgg cttggacaat agggcatttg aatcaaataa
 841 aaagaggagt aaacatgaaa atacgaataa aaagtccaaa caaagagaca ataaacagag
 901 aggtatcaat tttgagacac agttaccaaa aagaaatcca ggccaaagaa acaatgaagg
 961 aggtactctc tgacaacatg gaagtattga gtgaccacat aataattgag gggctttctg
1021 ccgaagagat aataaaaatg ggtgaaacag ttttggagat agaagaattg cattaa
```

FIGURE 7. Human Respiratory Syncytial Virus A, M Gene; GenBank Accession No. M74568 (SEQ ID NO: 7)

```
3241 aaggaaaggg tggggcaaat atggaaacat acgtgaacaa gcttcacgaa ggctccacat
3301 acacagctgc tgttcaatac aatgtcttag aaaaagacga tgaccctgca tcacttacaa
3361 tatgggtgcc catgttccaa tcatctatgc cagcagattt acttataaaa gaactagcta
3421 atgtcaacat actagtgaaa caaatatcca cacccaaggg accttcacta agagtcatga
3481 taaactcaag aagtgcagtg ctagcacaaa tgcccagcaa atttaccata tgcgctaatg
3541 tgtccttgga tgaaagaagc aaactagcat atgatgtaac cacaccctgt gaaatcaagg
3601 catgtagtct aacatgccta aaatcaaaaa atatgttgac tacagttaaa gatctcacta
3661 tgaagacact caaccctaca catgatatta ttgctttatg tgaatttgaa aacatagtaa
3721 catcaaaaaa agtcataata ccaacatacc taagatccat cagtgtcaga aataaagatc
3781 tgaacacact tgaaaatata acaaccactg aattcaaaaa tgctatcaca aatgcaaaaa
3841 tcatcccta ctcaggatta ctattagtca tcacagtgac tgacaacaaa ggagcattca
3901 aatacataaa gccacaaagt caattcatag tagatcttgg agcttaccta gaaaaagaaa
3961 gtatatatta tgttaccaca aattggaagc acacagctac acgatttgca atcaaaccca
4021 tggaagatta accttttcc tctacatcag tgtgttaatt catacaaact ttctacctac
4081 attcttcact tcaccatcac aatcacaaac actctgtggt tcaaccaatc aaacaaaact
4141 tatctgaagt cccagatcat cccaagtcat tgtttatcag atctagtact caaataagtt
4201 aataaaaat atacacatgg ggcaaataat cattggagga atccaacta atcacaatat
```

FIGURE 8. Human Respiratory Syncytial Virus A, M Gene; GenBank Accession No. U50363 (SEQ ID NO: 8)

```
3241 aaggaaaggg tggggcaaat atggaaacat acgtgaacaa gcttcacgaa ggctccacat
3301 acacagctgc tgttcaatac aatgtcttag aaaaagacga tgaccctgca tcacttacaa
3361 tatgggtgcc catgttccaa tcatctatgc cagcagattt acttataaaa gaactagcta
3421 atgtcaacat actagtgaaa caaatatcca cacccaaggg accttcacta agagtcatga
3481 taaactcaag aagtgcagtg ctagcacaaa tgcccagcaa atttaccata tgcgctaatg
3541 tgtccttgga tgaaagaagc aaactagcat atgatgtaac cacaccctgt gaaatcaagg
3601 catgtagtct aacatgccta aaatcaaaaa atatgttgac tacagttaaa gatctcacta
3661 tgaagacact caaccctaca catgatatta ttgctttatg tgaatttgaa aacatagtaa
3721 catcaaaaaa agtcataata ccaacatacc taagatccat cagtgtcaga aataaagatc
3781 tgaacacact tgaaaatata acaaccactg aattcaaaaa tgctatcaca aatgcaaaaa
3841 tcatccctta ctcaggatta ctattagtca tcacagtgac tgacaacaaa ggagcattca
3901 aatacataaa gccacaaagt caattcatag tagatcttgg agcttaccta gaaaaagaaa
3961 gtatatatta tgttaccaca aattggaagc acacagctac acgatttgca atcaaaccca
4021 tggaagatta accttttttcc tctacatcag tgtgttaatt catacaaaact ttctacctac
4081 attcttcact tcaccatcac aatcacaaac actctgtggt tcaaccaatc aaacaaaact
4141 tatctgaagt cccagatcat cccaagtcat tgtttatcag atctagtact caaataagtt
4201 aataaaaaat atacacatgg ggcaaataat cattggagga aatccaacta atcacaatat
```

FIGURE 9. Human Respiratory Syncytial Virus A, M Gene; GenBank Accession No. U50362 (SEQ ID NO: 9)

```
3241 aaggaaaggg tggggcaaat atggaaacat acgtgaacaa gcttcacgaa ggctccacat
3301 acacagctgc tgttcaatac aatgtcttag aaaaagacga tgaccctgca tcacttacaa
3361 tatgggtgcc catgttccaa tcatctatgc cagcagattt acttataaaa gaactagcta
3421 atgtcaacat actagtgaaa caaatatcca cacccaaggg accttcacta agagtcatga
3481 taaactcaag aagtgcagtg ctagcacaaa tgcccagcaa atttaccata tgcgctaatg
3541 tgtccttgga tgaaagaagc aaactagcat atgatgtaac cacacctgt gaaatcaagg
3601 catgtagtct aacatgccta aaatcaaaaa atatgttgac tacagttaaa gatctcacta
3661 tgaagacact caaccctaca catgatatta ttgctttatg tgaatttgaa aacatagtaa
3721 catcaaaaaa agtcataata ccaacatacc taagatccat cagtgtcaga aataaagatc
3781 tgaacacact tgaaaatata acaaccactg aattcaaaaa tgctatcaca aatgcaaaaa
3841 tcatcccctta ctcaggatta ctattagtca tcacagtgac tgacaacaaa ggagcattca
3901 aatacataaa gccacaaagt caattcatag tagatcttgg agcttaccta gaaaaagaaa
3961 gtatatatta tgttaccaca aattggaagc acacagctac acgatttgca atcaaaccca
4021 tggaagatta accttttttcc tctacatcag tgtgttaatt catacaaact ttctacctac
4081 attcttcact tcaccatcac aatcacaaac actctgtggt tcaaccaatc aaacaaaact
4141 tatctgaagt cccagatcat cccaagtcat tgtttatcag atctagtact caaataagtt
4201 aataaaaaat atacacatgg ggcaaataat cattggagga atccaacta atcacaatat
```

FIGURE 10. Human Respiratory Syncytial Virus B, M Gene; GenBank Accession No. NC_001781 (SEQ ID NO: 10)

```
3241 aaaagaacaa gatggggcaa atatggaaac atacgtgaac aagcttcacg aaggctccac
3301 atacacagca gctgttcagt acaatgttct agaaaaagat gatgatcctg catcactaac
3361 aatatgggtg cctatgttcc agtcatctgt accagcagac ttgctcataa aagaacttgc
3421 aagcatcaac atactagtga agcagatctc tacgcccaaa ggaccttcac tacgagtcac
3481 gattaactca agaagtgctg tgctggctca aatgcctagt aatttcatca taagcgcaaa
3541 tgtatcatta gatgaaagaa gcaaattagc atatgatgta actacacctt gtgaaatcaa
3601 agcatgcagt ctaacatgct taaaagtgaa aagtatgtta actacagtca aagatcttac
3661 catgaagaca ttcaacccca ctcatgagat cattgctcta tgtgaatttg aaaatattat
3721 gacatcaaaa agagtaataa taccaaccta tctaagacca attagtgtca aaacaagga
3781 tctgaactca ctagaaaaca tagcaaccac cgaattcaaa aatgctatca ccaatgcgaa
3841 aattattccc tatgctggat tagtattagt tatcacagtt actgacaata aaggagcatt
3901 caaatatatc aagccacaga gtcaatttat agtagatctt ggtgcctacc tagaaaaaga
3961 gagcatatat tatgtgacta ctaattggaa gcatacagct acacgttttt caatcaaacc
4021 actagaggat taaatttaat tatcaacact gaatgacagg tccacatata tcctcaaact
```

FIGURE 11. Human Respiratory Syncytial Virus B, M Gene; GenBank Accession No. AF013254 (SEQ ID NO: 11)

```
3241 aaaagaacaa gatggggcaa atatggaaac atacgtgaac aagcttcacg aaggctccac
3301 atacacagca gctgttcagt acaatgttct agaaaaagat gatgatcctg catcactaac
3361 aatatgggtg cctatgttcc agtcatctgt accagcagac ttgctcataa aagaacttgc
3421 aagcatcaac atactagtga agcagatctc tacgcccaaa ggaccttcac tacgagtcac
3481 gattaactca agaagtgctg tgctggctca aatgctagt aatttcatca taagcgcaaa
3541 tgtatcatta gatgaaagaa gcaaattagc atatgatgta actacaccttt gtgaaatcaa
3601 agcatgcagt ctaacatgct taaaagtgaa aagtatgtta actacagtca aagatcttac
3661 catgaagaca ttcaacccca ctcatgagat cattgctcta tgtgaatttg aaaatattat
3721 gacatcaaaa agagtaataa taccaaccta tctaagacca attagtgtca aaaacaagga
3781 tctgaactca ctagaaaaca tagcaaccac cgaattcaaa aatgctatca ccaatgcgaa
3841 aattattccc tatgctggat tagtattagt tatcacagtt actgacaata aaggagcatt
3901 caaatatatc aagccacaga gtcaatttat agtagatctt ggtgcctacc tagaaaaaga
3961 gagcatatat tatgtgacta ctaattggaa gcatacagct acacgttttt caatcaaacc
4021 actagaggat taaatttaat tatcaacact gaatgacagg tccacatata tcctcaaact
```

FIGURE 12. Human Respiratory Syncytial Virus B, M Gene; GenBank Accession No. AF013255 (SEQ ID NO: 12)

```
3241 aaaagaacaa gatggggcaa atatggaaac atacgtgaac aagcttcacg aaggctccac
3301 atacacagca gctgttcagt acaatgttct agaaaaagat gatgatcctg catcactaac
3361 aatatgggtg cctatgttcc agtcatctgt accagcagac ttgctcataa aagaacttgc
3421 aagcatcaac atactagtga agcagatctc tacgcccaaa ggaccttcac tacgagtcac
3481 gattaactca agaagtgctg tgctggctca aatgcctagt aatttcatca taagcgcaaa
3541 tgtatcatta gatgaaagaa gcaaattagc atatgatgta actacacctt gtgaaatcaa
3601 agcatgcagt ctaacatgct taaaagtgaa aagtatgtta actacagtca aagatcttac
3661 catgaagaca ttcaacccca ctcatgagat cattgctcta tgtgaatttg aaaatattat
3721 gacatcaaaa agagtaataa taccaaccta tctaagacca attagtgtca aaaacaagga
3781 tctgaactca ctagaaaaca tagcaaccac cgaattcaaa aatgctatca ccaatgcgaa
3841 aattattccc tatgctggat tagtattagt tatcacagtt actgacaata aaggagcatt
3901 caaatatatc aagccacaga gtcaatttat agtagatctt ggtgcctacc tagaaaaaga
3961 gagcatatat tatgtgacta ctaattggaa gcatacagct acacgttttt caatcaaacc
4021 actagaggat taaatttaat tatcaacact gaatgacagg tccacatata tcctcaaact
```

MULTIPLEX DETECTION ASSAY FOR INFLUENZA AND RSV VIRUSES

CROSS-REFERENCE TO RELATED APPLICATIONS

This application is a Divisional of U.S. application Ser. No. 11/963,699, filed Dec. 21, 2007, which issued as U.S. Pat. No. 8,354,230, on Jan. 15, 2013.

FIELD OF THE INVENTION

The present invention relates generally to the field of pathogen detection. In particular, the present invention relates to methods of detecting Influenza A (Flu A), Influenza B (Flu B), Respiratory Syncytial Virus A (RSV A), and Respiratory Syncytial Virus B (RSV B) in a sample.

BACKGROUND OF THE INVENTION

The following description is provided to assist the understanding of the reader. None of the information provided or references cited is admitted to be prior art to the present invention.

Influenza is a highly contagious viral infection of the nose, throat, and lungs. Influenza occurs most often in late fall, winter, and early spring. On average, 1:10 adults and 1:3 children catch influenza every year. In North America, Europe and Japan alone, 100 million people are infected with influenza each year. Influenza causes a 30-50% increase in primary care consultations. Amantidine (Symmetrel) is effective against influenza A if given early in the illness. However, resistance to amantidine emerges rapidly. Ribavirin is thought to be effective against both influenza A and B. Neuraminidase inhibitors (Relenza and Tamiflu) are highly effective and have fewer side effects than amantidine. In addition, resistance to these agents emerges slowly. The influenza virus is a single-stranded negative-sense RNA enveloped virus with hemagglutinin and neuraminidase viral envelope proteins.

RSV is the most common cause of bronchiolitis and pneumonia among infants and children under 1 year old. Often mistaken for the flu or the common cold, RSV emerges in the winter months, beginning with a fever and runny nose, then developing into a cough. It is estimated that 1 out of every 2 infants under age one will be infected by RSV. RSV circulates through direct physical contact as well as through airborne droplets released during coughing or sneezing. It also survives for several hours on household objects. Aerosolized Ribavirin can be used for infants with severe infection, and for those at risk of severe disease. RSV immunoglobulin can also be used to protect infants at risk of severe RSV disease. RSV is a single-stranded negative-sense RNA enveloped virus. The RSV genome encodes at least 10 viral proteins.

SUMMARY OF THE INVENTION

The present invention provides compositions and methods for determining the presence or absence of Influenza A, Influenza B, RSV A, and RSV B in a sample. The invention may also be used alone, or in combination with clinical symptoms or other indicators, for diagnosing an individual as having influenza or RSV. Specifically, the present invention enables the detection of pathogens known to cause influenza or RSV by detecting the presence of nucleic acids in the sample. The detection methodology is based on the discovery of particular target sequences within the genome which are useful indicators of infection. The present invention generally relates to a molecular test of Flu A, Flu B, RSV A, and RSV B to identify patients with viral infection.

Accordingly, in one aspect, methods are provided for identifying the presence or absence of a viral pathogen in a sample by detecting the presence or absence of the RSV A M gene or fragment thereof; or the RSV B M gene or fragment thereof in the sample. The presence of the RSV A M gene or fragment thereof in the sample indicates that the sample contains the pathogen RSV A, while the presence of the RSV B M gene or fragment thereof in the sample indicates that the sample contains the pathogen, RSV B.

In a second aspect, methods are provided for diagnosing a subject for infection with a respiratory syncytial viral pathogen, by evaluating a biological sample from the subject for the presence or absence of the RSV A M gene or fragment thereof; or the RSV B M gene or fragment thereof; wherein the presence of the pathogenic gene or fragment thereof indicates that the individual is infected with the associated organism.

In preferred embodiments, the step of detecting or evaluating includes (a) contacting a sample with one or more primers suitable for amplifying the gene or fragment thereof; (b) performing a primer extension reaction containing the primers of step (a) under conditions suitable to a produce reaction product from the gene or fragment thereof if the gene or fragment thereof is present in the sample; and (c) detecting the presence or absence of the reaction product, thereby determining the presence or absence of a viral pathogen in the sample.

In a third aspect, methods are provided for identifying the presence or absence of a viral pathogen in a sample by detecting the presence or absence of any two or more of: (a) the Influenza A M gene or fragment thereof; (b) the Influenza B M gene or fragment thereof; (c) the RSV A M gene or fragment thereof; and (d) the RSV B M gene or fragment thereof; but not (a) and (b) only, in which the presence of one or more of the genes or fragments specified in (a), (b), (c), or (d) indicates that the biological sample contains the associated pathogen.

In a fourth aspect, methods are provided for diagnosing a subject for infection with an influenza or respiratory syncytial viral pathogen, by evaluating a biological sample from the subject for the presence or absence of any two or more of: (a) the Influenza A M gene or fragment thereof; (b) the Influenza B M gene or fragment thereof; (c) the RSV A M gene or fragment thereof; and (d) the RSV B M gene or fragment thereof; but not (a) and (b) only, wherein the presence of one or more of the genes or fragments thereof specified in (a), (b), (c), or (d) indicates that the individual is infected with the associated organism.

In preferred embodiments, the step of detecting or evaluating includes (a) contacting a sample with one or more primers suitable for amplifying the genes or fragments thereof; (b) performing a multiplex primer extension reaction containing the primers of step (a) under conditions suitable to produce reaction products from the genes or fragments thereof if the genes or fragments thereof are present in the sample; and (c) detecting the presence or absence of one or more of the reaction products, thereby determining the presence or absence of a viral pathogen in the sample.

As used herein, unless otherwise stated, the singular forms "a," "an," and "the" include plural reference. Thus, for example, a reference to "an oligonucleotide" includes a plurality of oligonucleotide molecules, and a reference to "a nucleic acid" is a reference to one or more nucleic acids.

As used herein, "about" means plus or minus 10% unless otherwise indicated.

By "pathogen" is meant any microbial organism capable of causing influenza or RSV or a related condition in a mammal (e.g., a human). Specific pathogens include, for example, Influenza A, Influenza B, RSV A, and RSV B.

As used herein, the term "sample" or "test sample" may include clinical samples, isolated nucleic acids, or isolated microorganisms. In preferred embodiments, a sample is obtained from a biological source (i.e., a "biological sample"), such as tissue, bodily fluid, or microorganisms collected from a subject. Sample sources include, but are not limited to, mucus, sputum (processed or unprocessed), bronchial alveolar lavage (BAL), bronchial wash (BW), blood, bodily fluids, cerebrospinal fluid (CSF), urine, plasma, serum, or tissue (e.g., biopsy material). The term "patient sample" as used herein refers to a sample obtained from a human seeking diagnosis and/or treatment of a disease. Preferred sample sources include nasal swabs or washes.

"Genomic nucleic acid" or "genomic DNA" refers to some or all of the DNA from a chromosome. Genomic DNA may be intact or fragmented (e.g., digested with restriction endonucleases by methods known in the art). In some embodiments, genomic DNA may include sequence from all or a portion of a single gene or from multiple genes. In contrast, the term "total genomic nucleic acid" is used herein to refer to the full complement of DNA contained in the genome. Methods of purifying DNA and/or RNA from a variety of samples are well-known in the art.

As used herein, the term "oligonucleotide" refers to a short polymer composed of deoxyribonucleotides, ribonucleotides or any combination thereof. Oligonucleotides are generally between about 10, 11, 12, 13, 14 or 15 to about 150 nucleotides in length, more preferably about 10, 11, 12, 13, 14, or 15 to about 70 nucleotides, and most preferably between about 15 to about 40 nucleotides in length. The single letter code for nucleotides is as described in the U.S. Patent Office Manual of Patent Examining Procedure, section 2422, table 1. In this regard, the nucleotide designation "R" means purine such as guanine or adenine, "Y" means pyrimidine such as cytosine or thymidine (uracil if RNA); and "M" means adenine or cytosine. An oligonucleotide may be used as a primer or as a probe.

The term "target nucleic acid" or "target sequence" as used herein refers to a sequence which includes a segment of nucleotides of interest to be amplified and detected. Copies of the target sequence which are generated during the amplification reaction are referred to as amplification products, amplimers, or amplicons. Target nucleic acid may be composed of segments of a chromosome, a complete gene with or without intergenic sequence, segments or portions of a gene with or without intergenic sequence, or sequences of nucleic acids for which probes or primers are designed. Target nucleic acids may include a wild-type sequence(s), a mutation, deletion or duplication, tandem repeat regions, a gene of interest, a region of a gene of interest or any upstream or downstream region thereof. Target nucleic acids may represent alternative sequences or alleles of a particular gene. Target nucleic acids may be derived from genomic DNA, cDNA, or RNA. As used herein target nucleic acid may be DNA or RNA extracted from a cell or a nucleic acid copied or amplified therefrom, or may include extracted nucleic acids further converted using a bisulfite reaction.

A "fragment" in the context of a nucleic acid refers to a sequence of nucleotide residues which are at least about 5 nucleotides, at least about 7 nucleotides, at least about 9 nucleotides, at least about 11 nucleotides, or at least about 15 nucleotides. The fragment is typically less than about 300 nucleotides, less than about 100 nucleotides, less than about 75 nucleotides, less than about 50 nucleotides, or less than 40 nucleotides. In certain embodiments, the fragments can be used in polymerase chain reaction (PCR), various hybridization procedures, or microarray procedures to identify or amplify identical or related parts of mRNA or DNA molecules. A fragment or segment may uniquely identify each polynucleotide sequence of the present invention.

As used herein, the term "substantially identical", when referring to a nucleic acid, is one that has at least 80%, 85%, 90%, 95%, or 99% sequence identify to a reference nucleic acid sequence. The length of comparison is preferably the full length of the nucleic acid, but is generally at least 15 nucleotides, 20 nucleotides, 30 nucleotides, 40 nucleotides, 50 nucleotides, 75 nucleotides, 100 nucleotides, 125 nucleotides, or more.

By "isolated", when referring to a nucleic acid (e.g., an oligonucleotide) is meant a nucleic acid that is apart from a substantial portion of the genome in which it naturally occurs. For example, any nucleic acid that has been produced synthetically (e.g., by serial base condensation) is considered to be isolated. Likewise, nucleic acids that are recombinantly expressed, produced by a primer extension reaction (e.g., PCR), or otherwise excised from a genome are also considered to be isolated.

The term "complement" "complementary" or "complementarity" as used herein with reference to polynucleotides (i.e., a sequence of nucleotides such as an oligonucleotide or a target nucleic acid) refers to standard Watson/Crick pairing rules. The complement of a nucleic acid sequence such that the 5' end of one sequence is paired with the 3' end of the other, is in "antiparallel association." For example, the sequence "5'-A-G-T-3'" is complementary to the sequence "3'-T-C-A-5'." Certain bases not commonly found in natural nucleic acids may be included in the nucleic acids described herein; these include, for example, inosine, 7-deazaguanine, Locked Nucleic Acids (LNA), and Peptide Nucleic Acids (PNA). Complementarity need not be perfect; stable duplexes may contain mismatched base pairs, degenerative, or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs. A complement sequence can also be a sequence of RNA complementary to the DNA sequence or its complement sequence, and can also be a cDNA. The term "substantially complementary" as used herein means that two sequences specifically hybridize (defined below). The skilled artisan will understand that substantially complementary sequences need not hybridize along their entire length.

As used herein, an oligonucleotide is "specific" for a nucleic acid if the oligonucleotide has at least 50% sequence identity with a portion of the nucleic acid when the oligonucleotide and the nucleic acid are aligned. An oligonucleotide that is specific for a nucleic acid also is one that, under the appropriate hybridization or washing conditions, is capable of hybridizing to the target of interest and not substantially hybridizing to nucleic acids which are not of interest. Higher levels of sequence identity are preferred and include at least 75%, at least 80%, at least 85%, at least 90%, at least 95% and more preferably at least 98% sequence identity. Sequence identity can be determined using a commercially available computer program with a default setting that employs algorithms well known in the art (e.g., BLAST). As used herein, sequences that have "high sequence identity" have identical nucleotides at least at about 50% of aligned nucleotide positions, preferably at least at about 60% of aligned nucleotide positions, and more preferably at least at about 75% of aligned nucleotide positions.

An oligonucleotide (e.g., a probe or a primer) that is specific for a target nucleic acid will "hybridize" to the target nucleic acid under suitable conditions. As used herein, "hybridization" or "hybridizing" refers to the process by which an oligonucleotide single strand anneals with a complementary strand through base pairing under defined hybridization conditions.

"Specific hybridization" is an indication that two nucleic acid sequences share a high degree of complementarity. Specific hybridization complexes form under permissive annealing conditions and remain hybridized after any subsequent washing steps. Permissive conditions for annealing of nucleic acid sequences are routinely determinable by one of ordinary skill in the art and may occur, for example, at 65° C. in the presence of about 6×SSC. Stringency of hybridization may be expressed, in part, with reference to the temperature under which the wash steps are carried out. Such temperatures are typically selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Equations for calculating $T_m$ and conditions for nucleic acid hybridization are known in the art.

Oligonucleotides used as primers or probes for specifically amplifying (i.e., amplifying a particular target nucleic acid sequence) or specifically detecting (i.e., detecting a particular target nucleic acid sequence) a target nucleic acid generally are capable of specifically hybridizing to the target nucleic acid.

The term "amplification" or "amplify" as used herein includes methods for copying a target nucleic acid, thereby increasing the number of copies of a selected nucleic acid sequence. Amplification may be exponential or linear. A target nucleic acid may be either DNA or RNA. The sequences amplified in this manner form an "amplicon" or "amplification product". While the exemplary methods described hereinafter relate to amplification using the polymerase chain reaction (PCR), numerous other methods are known in the art for amplification of nucleic acids (e.g., isothermal methods, rolling circle methods, etc.). The skilled artisan will understand that these other methods may be used either in place of, or together with, PCR methods. See, e.g., Saiki, "Amplification of Genomic DNA" in *PCR Protocols*, Innis et al., Eds., Academic Press, San Diego, Calif. 1990, pp 13-20; Wharam, et al., *Nucleic Acids Res.* 2001 Jun. 1; 29(11):E54-E54; Hafner, et al., *Biotechniques* 2001 April; 30(4):852-6, 858, 860; Zhong, et al., *Biotechniques* 2001 April; 30(4):852-6, 858, 860.

As used herein, the term "detecting" used in the context of detecting a signal from a detectable label to indicate the presence of a target nucleic acid in the sample does not require the method to provide 100% sensitivity and/or 100% specificity. As is well known, "sensitivity" is the probability that a test is positive, given that the subject has a target nucleic acid sequence, while "specificity" is the probability that a test is negative, given that the subject does not have the target nucleic acid sequence. A sensitivity of at least 50% is preferred, although sensitivities of at least 60%, at least 70%, at least 80%, at least 90% and at least 99% are clearly more preferred. A specificity of at least 50% is preferred, although sensitivities of at least 60%, at least 70%, at least 80%, at least 90% and at least 99% are clearly more preferred. Detecting also encompasses assays with false positives and false negatives. False negative rates may be 1%, 5%, 10%, 15%, 20% or even higher. False positive rates may be 1%, 5%, 10%, 15%, 20% or even higher.

As used herein, a "primer" for amplification is an oligonucleotide that is complementary to a target nucleotide sequence and leads to addition of nucleotides to the 3' end of the primer in the presence of a DNA or RNA polymerase. The 3' nucleotide of the primer should generally be identical to the target sequence at a corresponding nucleotide position for optimal expression and/or amplification. The term "primer" as used herein includes all forms of primers that may be synthesized including peptide nucleic acid primers, locked nucleic acid primers, phosphorothioate modified primers, labeled primers, and the like. As used herein, a "forward primer" is a primer that is complementary to the anti-sense strand of dsDNA. A "reverse primer" is complementary to the sense-strand of dsDNA. A "primer pair" refers to the combination of a forward primer and a reverse primer, each specific for the same target nucleic acid.

As used herein, "Scorpion primer" or "Scorpion probe" refers to an oligonucleotide having a 3' primer with a 5' extended probe tail having a hairpin structure which possesses a fluorophore/quencher pair. Optionally, the Scorpion primer/probe further contains an amplification blocker (e.g., hexethylene glycol ("HEG") separating the probe moiety from the primer moiety.

As used herein, the term "Scorpion detection system" refers to a method for real-time PCR. This method utilizes a bi-functional molecule (referred to herein as a "Scorpion"), which contains a PCR primer element covalently linked by a polymerase-blocking group to a probe element. Additionally, each Scorpion molecule contains a fluorophore that interacts with a quencher to reduce the background fluorescence.

As used herein "TaqMan® PCR detection system" refers to a method for real time PCR. In this method, a TaqMan® probe which hybridizes to the nucleic acid segment amplified is included in the PCR reaction mix. The TaqMan® probe includes a donor and a quencher fluorophore on either end of the probe and in close enough proximity to each other so that the fluorescence of the donor is taken up by the quencher. However, when the probe hybridizes to the amplified segment, the 5'-exonuclease activity of the Taq polymerase cleaves the probe thereby allowing the donor fluorophore to emit fluorescence which can be detected.

By "primer extension reaction" is meant a synthetic reaction in which an oligonucleotide primer hybridizes to a target nucleic acid and a complementary copy of the target nucleic acid is produced by the polymerase-dependent 3'-addition of individual complementary nucleotides. In preferred embodiments, the primer extension reaction is PCR.

The term "multiplex primer extension reaction" as used herein refers to a primer extension reaction that is capable of simultaneously producing complementary copies of two or more target nucleic acids within the same reaction vessel. Each reaction product is primed using a distinct primer pair. A multiplex reaction may further include specific probes for each product that are detectably labeled with different detectable moieties. In preferred embodiments, the multiplex primer extension reaction is a multiplex PCR in which two or more products within the same reaction vessel are amplified.

By "suitable for amplifying," when referring to oligonucleotide primer or primer pairs, is meant primers that specifically hybridize to a target nucleic acid and are capable of providing an initiation site for a primer extension reaction in which a complementary copy of the target nucleic acid is synthesized.

In a fifth aspect, the invention provides target nucleic acids for pathogens capable of causing influenza A, influenza B, RSV A, and/or RSV B. Specifically, the invention provides isolated nucleic acid(s) that are at least about 90% identical (e.g., about 95% identical, about 99% identical, or 100% identical) to at least 20 contiguous nucleotides (e.g., 25, 30, 35, 40, 50, 75, 90, or more) of the sequence of SEQ ID NOs: 32, 33, 34, or 35, or complements thereof. In a preferred embodiment, the target nucleic acids are less than about 300, 250, 200, 175, 150, or 125 contiguous nucleotides in length. In one preferred embodiment, the target nucleic acids contain a nucleotide sequence that is substantially identical to at least 20 contiguous nucleotides of SEQ ID NOs: 32, 33, 34, or 35, or complements thereof. In a particularly preferred embodiment, the target nucleic acids contain a nucleotide sequence of SEQ ID NOs: 32, 33, 34, or 35, or complements thereof.

In a sixth aspect, the invention provides a kit containing at least two or more of (a), (h), (c), or (d) but not (a) and (b) only in which: (a) is one or more primers suitable for detecting or amplifying an Influenza A M gene or fragment thereof and a first probe capable of specifically hybridizing to the Influenza A M gene or fragment thereof; (b) is one or more primers suitable for detecting or amplifying an Influenza B M gene or fragment thereof and a second probe capable of specifically hybridizing to the Influenza B M gene or fragment thereof; (c) is one or more primers suitable for detecting or amplifying a RSV A M gene or fragment thereof and a third probe capable of specifically hybridizing to the RSV A M gene or fragment thereof; and (d) is one or more primers suitable for detecting or amplifying a RSV B M gene or fragment thereof and a fourth probe capable of specifically hybridizing to the RSV B M gene or fragment thereof; in which the first, second, third, and fourth probe further include detectable labels.

In certain embodiments of the above aspects, methods are provided for amplifying (e.g., by PCR) one, two, three or all four of the genes and/or fragments. Preferably, the genes and/or fragments are detected simultaneously, and more preferably, in a multiplex real-time PCR assay. Most preferably, amplification and detection are performed in a single reaction.

In preferred embodiments of the above aspects, the Influenza A M gene fragment is a nucleic acid having at least 20 contiguous nucleotides that are substantially identical to the sequence of SEQ ID NO: 32, or a complement thereof. Preferably, the Influenza A M gene or fragment is amplified using one or more primers containing the sequence of: SEQ ID NOs: 13, 14, 15, or complements thereof. In other preferred embodiments, the Influenza A M gene or fragment is detected using an oligonucleotide probe containing the sequence of SEQ ID NO: 16, 40 or complements thereof. The oligonucleotide probe is preferably labeled with a detectable fluorescent marker.

In other preferred embodiments of the above aspects, the Influenza B M gene fragment is a nucleic acid having at least 20 contiguous nucleotides that are substantially identical to the sequence of SEQ ID NO: 33, or a complement thereof. Preferably, the Influenza B M gene or fragment is amplified using one or more primers containing the sequence of: SEQ ID NOs: 17, 18, 19, or complements thereof. In other preferred embodiments, the Influenza B M gene or fragment is detected using an oligonucleotide probe containing the sequence of SEQ ID NO: 20, or a complement thereof. The oligonucleotide probe is preferably labeled with a detectable fluorescent marker.

In other preferred embodiments of the above aspects, the RSV A M gene fragment is a nucleic acid having at least 20 contiguous nucleotides that are substantially identical to the sequence of SEQ ID NO: 34, or a complement thereof. Preferably, the RSV A M gene or fragment is amplified using one or more primers containing the sequence of: SEQ ID NOs: 21, 22, 23, or complements thereof. In other preferred embodiments, the RSV A M gene or fragment is detected using an oligonucleotide probe containing the sequence of SEQ ID NO: 24, or a complement thereof. The oligonucleotide probe is preferably labeled with a detectable fluorescent marker.

In other preferred embodiments of the above aspects, the RSV B M gene fragment is a nucleic acid having at least 20 contiguous nucleotides that are substantially identical to the sequence of SEQ ID NO: 35, or a complement thereof. Preferably, the RSV B M gene or fragment is amplified using one or more primers containing the sequence of: SEQ ID NOs: 25, 26, 27, or complements thereof. In other preferred embodiments, the RSV B M gene or fragment is detected using an oligonucleotide probe containing the sequence of SEQ ID NO: 28, or a complement thereof. The oligonucleotide probe is preferably labeled with a detectable fluorescent marker.

In certain preferred embodiments of the above aspects, one or more of the primers suitable for amplifying the genes or fragments is a Scorpion primer. Preferably, the Scorpion primer includes an oligonucleotide probe sequence and an oligonucleotide primer sequence each of which individually conform to the requirements of an oligonucleotide primer and probe, respectively. More preferably, the Scorpion primers have the sequence of SEQ ID NOs: 15, 19, 23, 27, or complements thereof.

In some preferred embodiments of the above aspects, the primers and probes of the invention are 10-50 (e.g., 12, 14, 16, 18, 20, 22, 25, 30, 35, 40, or 45) nucleotides in length and are substantially identical, preferably 100% identical to the corresponding sequences of SEQ ID NOs 32, 33, 34, or 35, or complements thereof. More preferably, the primers and probes have a nucleotide sequence of SEQ ID NOs: 13, 14, 16, 17, 18, 20, 21, 22, 24, 25, 26, 28, 40 or complements thereof. In preferred embodiments, the probe is an oligonucleotide complementary to the target sequence.

In other preferred embodiments of the above aspects, the gene fragments consist of at least 15, at least 20, at least 30, at least 40, at least 50, at least 75, at least 100 nucleotides that have a nucleotide sequence that is substantially identical or identical to the nucleotide sequence of the reference gene.

It is recognized that any of the foregoing genes or fragments may be assayed individually to identify the individual pathogens, or may be assayed in combination with each other (e.g., any two, any three, or all four genes) and/or with other biological indicators (e.g., proteins, nucleic acids, antigens, etc.) for the same or different organisms. Furthermore, any of the foregoing methods, alone or in combination with clinical evaluation or other diagnostic methods (e.g. lung X-ray), may be used to diagnose an individual as having influenza A, influenza B, RSV A, and/or RSV B.

Units, prefixes, and symbols may be denoted in their accepted S1 form. Unless otherwise indicated, nucleic acids are written left to right in 5' to 3' orientation; amino acid sequences are written left to right in amino to carboxy orientation. Amino acids may be referred to herein by either their commonly known three letter symbols or by the one-letter symbols recommended by the IUPAC-IUBMB Nomenclature Commission. Nucleotides, likewise, may be referred to by their commonly accepted single-letter codes.

BRIEF DESCRIPTION OF THE FIGURES

FIG. 1 is a nucleotide sequence of the Influenza A Virus Matrix Protein 1 and Matrix Protein 2 Genes, Segment 7 (M gene) provided at GenBank Accession No. CY002353 (SEQ ID NO: 1).

FIG. 2 is a nucleotide sequence of the Influenza A Virus Matrix Protein 1 and Matrix Protein 2 Genes, Segment 7 (M gene) provided at GenBank Accession No. CY002985 (SEQ ID NO: 2)

FIG. 3 is a nucleotide sequence of the Influenza A Virus Matrix Protein 1 and Matrix Protein 2 Genes, Segment 7 (M gene) provided at GenBank Accession No. CY002057 (SEQ ID NO: 3)

FIG. 4 is a nucleotide sequence of the Influenza B Virus M1 Matrix Protein and BM2 Protein Genes (M gene) provided at GenBank Accession No. AY581982 (SEQ ID NO:4).

FIG. 5 is a nucleotide sequence of the Influenza B Virus M1 Matrix Protein and BM2 Protein Genes (M gene) provided at GenBank Accession No. AY581981 (SEQ ID NO:5).

FIG. 6 is a nucleotide sequence of the Influenza B Virus M1 Matrix Protein and BM2 Protein Genes (M gene) provided at GenBank Accession No. AY581980 (SEQ ID NO:6).

FIG. 7 is a nucleotide sequence of the Human Respiratory Syncytial Virus A M gene sequence provided at GenBank Accession No. M74568 (SEQ ID NO:7).

FIG. 8 is a nucleotide sequence of the Human Respiratory Syncytial Virus A M gene sequence provided at GenBank Accession No. U50363 (SEQ ID N0:8).

FIG. 9 is a nucleotide sequence of the Human Respiratory Syncytial Virus A M gene sequence provided at GenBank Accession No. U50362 (SEQ ID NO:9).

FIG. 10 is nucleotide sequence of the Human Respiratory Syncytial Virus B M gene sequence provided at GenBank Accession No. NC_001781 (SEQ ID NO:10).

FIG. 11 is nucleotide sequence of the Human Respiratory Syncytial Virus 13 M gene sequence provided at GenBank Accession No. AF013254 (SEQ ID NO:11).

FIG. 12 is nucleotide sequence of the Human Respiratory Syncytial Virus B M gene sequence provided at GenBank Accession No. AF013255 (SEQ ID NO:12).

DETAILED DESCRIPTION OF THE INVENTION

The present invention provides methods, compositions, and kits suitable for identifying pathogens capable of causing influenza and RSV in a sample that may contain nucleic acids from pathogenic organisms. The invention is based on the real-time PCR detection of target nucleic acids. The methods of the invention, in conjunction with other laboratory results and clinical information, may be used in the diagnosis of, for example, respiratory tract infection in subjects with a clinical suspicion of a viral Flu A, Flu B, RSV A and/or RSV B infection. In particular, methods are provided for detecting Influenza A, Influenza B, RSV A, and RSV B in a biological sample obtained from an individual. In one aspect, methods are provided for multiplex detection of two or more pathogens simultaneously.

Molecular amplification based assays have been verified to be superior to antigen and culture methods in the diagnosis of respiratory tract infections caused by RNA virus. Molecular assays have higher sensitivity and specificity with shorter turn around time compared to antigen and culture methods.

In various embodiments of the present invention, oligonucleotide primers and probes are used in the methods described herein to provide the viral pathogen assay. Thus, in certain embodiments, the invention relates to primer sequences that can be used to amplify target nucleic acids of Flu A, Flu B, RSV A, and RSV B, or a combination thereof in a multiplex reaction. In particular embodiments, the target nucleic acids include the M gene for Flu A, Flu B, RSV A, and RSV R. Particularly preferred embodiments include the 5' region of the RSV A and RSV B M genes.

In certain embodiments, the methods and kits utilize Scorpion technology and a reverse primer for the real-time PCR amplification and detection of the target nucleic acids, Scorpion technology utilizes a bi-functional molecule containing a PCR primer element covalently linked by a polymerase-blocking group to a probe element. Each molecule contains a quencher that interacts with a fluorophore. The target is amplified by the reverse primer and the primer portion of the Scorpion specific for that target. A fluorescent signal is generated after the separation of the fluorophore from the quencher as a result of the binding of the probe element of the Scorpion to the extended DNA fragment.

In some embodiments, the assay further includes an internal control (IC) to verify adequate processing of the target viruses and reaction setup and to monitor the presence of inhibition in the RT-PCR assay to avoid false negative results.

In one aspect, the invention relates to one or more substantially purified oligonucleotides having sequences selected from the primers, probes, and Scorpions shown in Table 1.

TABLE 1

Exemplary Primer and Scorpion Sequences for Pathogen Detection

| Primer Name | Sequence (5' to 3') | SEQ ID NO: |
|---|---|---|
| Flu A Forward | GCATTTTGGACAAAGCGTCTA | SEQ ID NO: 13 |
| Flu A Reverse | TCACCTCTGACTAAGGGGA | SEQ ID NO: 14 |
| Flu A Scorpion | Quencher-AGCCGTGCCCAGIGAGCGGCT-dye-GCATTTTGGACAAAGCGTCTA | SEQ ID NO: 15 |
| Flu A Probe (option A) | CCGTGCCCAGTGAGCGA | SEQ ID NO: 16 |

TABLE 1-continued

Exemplary Primer and Scorpion Sequences for Pathogen Detection

| Primer Name | Sequence (5' to 3') | SEQ ID NO: |
|---|---|---|
| Flu A Probe (option B) | CCGTGCCCAGTGAGCGG | SEQ ID NO: 40 |
| Flu B Forward | GCTGAATTTCCCATGGAGCTC | SEQ ID NO: 17 |
| Flu B Reverse | CAGAAGAGCTGCAAAGCAACA | SEQ ID NO: 18 |
| Flu B Scorpion | Quencher- AGGGGCAAAGGATGTAATGGAAGTGCCC CT-dye-GCTGAATTTCCCATGGAGCTC | SEQ ID NO: 19 |
| Flu B Probe | GGCAAAGGATGTAATGGAAGTGC | SEQ ID NO: 20 |
| RSV A Forward | TGCACTTCTTGAGTTTATCATGACTCTTA | SEQ ID NO: 21 |
| RSV A Reverse | CACGAAGGCTCCACATACACA | SEQ ID NO: 22 |
| RSV A Scorpion | Quencher- AGGGTGAAACAAATATCCACACCCT-dye- TGCACTTCTTGAGTTTATCATGACTCTTA | SEQ ID NO: 23 |
| RSV A Probe | GTGAAACAAATATCCACACCC | SEQ ID NO: 24 |
| RSV B Forward | GCTTGCAAGTTCTTTTATGAGCAA | SEQ ID NO: 25 |
| RSV B Reverse | CACGAAGGCTCCACATACACA | SEQ ID NO: 26 |
| RSV B Scorpion | Quencher- AGGCTGCCTATGTTCCAGTCATCTGTAC CAGCAGCCT-dye-GCTTGCAAGTTCTTTTATGAG CAA | SEQ ID NO: 27 |
| RSV B Probe | CTGCCTATGTTCCAGTCATCTGTRCCAGCAG | SEQ ID NO: 28 |
| IC Forward | ATTCGCCCTT TGTTTCGACCTA | SEQ ID NO: 29 |
| IC Reverse | CCGACGACTGACGAGCAA | SEQ ID NO: 30 |
| IC Scorpion | Quencher-TGCGAACTGGCAAGCT-dye-ATTCGCCCTT TGTTTCGACCTA | SEQ ID NO: 31 |
| IC Probe | TGCGAACTGGCAAGCT | SEQ ID NO: 39 |

Biological Sample Collection and Preparation

Specimens from which target nucleic acids can be detected and quantified with the methods of the present invention are from sterile and/or non-sterile sites. Sterile sites from which specimens can be taken are body fluids such as blood (whole blood, serum, plasma), urine, cerebrospinal fluid (CSF), synovial fluid, pleural fluid, pericardial fluid, intraocular fluid, tissue biopsies or endotracheal aspirates. Non-sterile sites from which specimens can be taken are e.g., sputum, stool, swabs from e.g. skin, inguinal, nasal, pharyngeal and/or throat.

In one embodiment, the method provides for the extraction of nucleic acids from the subject's nasal cavity for use as the testing template followed by one-step RT-PCR using reverse transcription to convert target RNA to cDNA followed by the simultaneous amplification and detection of the target template.

The nucleic acid (DNA and/or RNA) may be isolated from the sample according to any methods well known to those of skill in the art. If necessary, the sample may be collected or concentrated by centrifugation and the like. The cells of the sample may be subjected to lysis, such as by treatment with enzymes, heat surfactants, ultrasonication or a combination thereof. The lysis treatment is performed in order to obtain a sufficient amount of DNA derived from the viral pathogens, if present in the sample, to detect using polymerase chain reaction.

Various methods of DNA extraction are suitable for isolating the DNA. Suitable methods include phenol and chloroform extraction. See Maniatis et al., *Molecular Cloning, A Laboratory Manual*, 2d, Cold Spring Harbor Laboratory Press, page 16.54 (1989). Numerous commercial kits also yield suitable DNA including, but not limited to, QIAamp™ mini blood kit, QIAamp™ Mini Viral RNA kit, Agencourt Genfind™, Roche Cobas® Roche MagNA Pure® or phenol:chloroform extraction using Eppendorf Phase Lock Gels®.

In one embodiment, a nucleic acid isolation step is used that isolates both RNA and DNA in one reaction. In an alternate embodiment, RNA and DNA may be isolated independently and then combined for use in the methods of the invention. In yet another alternate embodiment, when only one type of nucleic acid is required to be isolated (such as when all the disease agents and secondary disease agents of interest have the same type of nucleic acid genome), nucleic acid isolation methods that isolate only RNA or DNA may be used. The nucleic acid isolation techniques and protocols described herein may be used to isolate nucleic acid from a variety of patient samples or sources.

In one embodiment, a dual RNA/DNA isolation method is used employing a trizol based reagent for initial isolation of RNA and DNA from patient samples. Upon contact with patient samples, the phenol and high salt reagents in the trizol effectively inactivate any disease agent or secondary disease agent that may be present in the patient sample. In order to allow for the dual isolation of RNA and DNA in the same phase with a single step, the pH of the trizol solution may be adjusted towards neutral (instead of acidic). After the RNA and DNA are isolated from the patient samples, a silica based column may be used to further isolate the RNA and DNA. The use of silica based columns allows for wash steps to be performed quickly and efficiently while minimizing the possibility of contamination. The wash steps may be used to remove PCR and RT-PCR inhibitors. The column method for nucleic acid purification is advantageous as it can be used with different types of patient samples and the spin and wash steps effectively remove PCR or RT-PCR inhibitors. In one embodiment, the nucleic isolation is carried out using the dual RNA/DNA isolation kit provided by QIAamp® Viral RNA Mini Spin Kit (Qiagen, Valencia, Calif.).

Target Nucleic Acids and Primers

In various embodiments of the present invention, oligonucleotide primers and probes are used in the methods described herein to amplify and detect target sequences of pathogens. In certain preferred embodiments, target nucleic acids include the M gene and fragments thereof of the Flu A, Flu B, RSV A', and/or RSV B genome. In addition, primers can also be used to amplify one or more control nucleic acid sequences. The target nucleic acids described herein may be detected singly or in a multiplex format, utilizing individual labels for each target.

The skilled artisan is capable of designing and preparing primers that are appropriate for amplifying a target sequence in view of this disclosure. The length of the amplification primers for use in the present invention depends on several factors including the nucleotide sequence identity and the temperature at which these nucleic acids are hybridized or used during in vitro nucleic acid amplification. The considerations necessary to determine a preferred length for an amplification primer of a particular sequence identity are well known to the person of ordinary skill in the art.

Primers that amplify a nucleic acid molecule can be designed using, for example, a computer program such as OLIGO (Molecular Biology Insights, Inc., Cascade, Colo.). Important features when designing oligonucleotides to be used as amplification primers include, but are not limited to, an appropriate size amplification product to facilitate detection (e.g., by electrophoresis or real-time PCR), similar melting temperatures for the members of a pair of primers, and the length of each primer (i.e., the primers need to be long enough to anneal with sequence-specificity and to initiate synthesis but not so long that fidelity is reduced during oligonucleotide synthesis). Typically, oligonucleotide primers are 15 to 40 nucleotides in length.

Designing oligonucleotides to be used as hybridization probes can be performed in a manner similar to the design of primers. As with oligonucleotide primers, oligonucleotide probes usually have similar melting temperatures, and the length of each probe must be sufficient for sequence-specific hybridization to occur but not so long that fidelity is reduced during synthesis. Oligonucleotide probes are generally 15 to 60 nucleotides in length.

In some embodiments, a mix of primers is provided having degeneracy at one or more nucleotide positions. Degenerate primers are used in PCR where variability exists in the target sequence, i.e. the sequence information is ambiguous. Typically, degenerate primers will exhibit variability at no more than about 4, no more than about 3, preferably no more than about 2, and most preferably, no more than about 1 nucleotide position.

Amplification of Nucleic Acids

Nucleic acid samples or target nucleic acids may be amplified by various methods known to the skilled artisan. Preferably, PCR is used to amplify nucleic acids of interest.

Briefly, in PCR, two primer sequences are prepared that are complementary to regions on opposite complementary strands of the marker sequence. An excess of deoxynucleotide triphosphates are added to a reaction mixture along with a DNA polymerase, e.g., Taq polymerase.

If the target sequence is present in a sample, the primers will bind to the sequence and the polymerase will cause the primers to be extended along the target sequence by adding on nucleotides. By raising and lowering the temperature of the reaction mixture, the extended primers will dissociate from the target nucleic acid to form reaction products, excess primers will bind to the target nucleic acid and to the reaction products and the process is repeated, thereby generating amplification products. Cycling parameters can be varied, depending on the length of the amplification products to be extended. An internal positive amplification control (IC) can be included in the sample, utilizing oligonucleotide primers and/or probes. The IC can be used to monitor both the conversion process and any subsequent amplification.

In a suitable embodiment, PCR is performed using a Scorpion primer/probe combination. Scorpion probes, as used in the present invention include a 3' primer with a 5' extended probe tail having a hairpin structure which possesses a fluorophore/quencher pair. The probe tail is "protected" from replication in the 5' to 3' direction by the inclusion of hexethylene glycol (HEG) which blocks the polymerase from replicating the probe. During the first round of amplification the 3' target-specific primer anneals to the target and is extended such that the Scorpion is now incorporated into the newly synthesized strand, which possesses a newly synthesized target region for the 5' probe. During the next round of denaturation and annealing, the probe region of the Scorpion hairpin loop will hybridize to the target, thus separating the fluorophore and quencher and creating a measurable signal. Such probes are described in Whitcombe et al., *Nature Biotech* 17: 804-807 (1999).

In one embodiment, the target nucleic acids are amplified in a multiplex amplification reaction. A variety of multiplex amplification strategies are known in the art and may be used with the methods of the invention. The multiplex amplification strategy may use PCR, RT-PCR or a combination thereof depending on the type of nucleic acid contained in the disease agent(s). For example, if an RNA genome is present, RT-PCR may be utilized. The PCR enzyme may be an enzyme with both a reverse transcription and polymerase function. Furthermore, the PCR enzyme may be capable of "hot start" reactions as is known in the art.

Detection of Amplified Nucleic Acids

Amplification of nucleic acids can be detected by any of a number of methods well-known in the art such as gel electrophoresis, column chromatography, hybridization with a probe, sequencing, melting curve analysis, or "real-time" detection.

In one approach, sequences from two or more fragments of interest are amplified in the same reaction vessel (i.e. "multiplex PCR"). Detection can take place by measuring the end-point of the reaction or in "real time." For real-time detection, primers and/or probes may be detectably labeled to allow differences in fluorescence when the primers become incorporated or when the probes are hybridized, for example, and amplified in an instrument capable of monitoring the change in fluorescence during the reaction. Real-time detection methods for nucleic acid amplification are well known and include, for example, the TaqMan® system, the Scorpion bi-functional molecule, and the use of intercalating dyes for double stranded nucleic acid.

In end-point detection, the amplicon(s) could be detected by first size-separating the amplicons, then detecting the size-separated amplicons. The separation of amplicons of different sizes can be accomplished by, for example, gel electrophoresis, column chromatography, or capillary electrophoresis. These and other separation methods are well-known in the art. In one example, amplicons of about 10 to about 150 base pairs whose sizes differ by 10 or more base pairs can be separated, for example, on a 4% to 5% agarose gel (a 2% to 3% agarose gel for about 150 to about 300 base pair amplicons), or a 6% to 10% polyacrylamide gel. The separated nucleic acids can then be stained with a dye such as ethidium bromide and the size of the resulting stained band or bands can be compared to a standard DNA ladder.

In another embodiment, two or more fragments of interest are amplified in separate reaction vessels. If the amplification is specific, that is, one primer pair amplifies for one fragment of interest but not the other, detection of amplification is sufficient to distinguish between the two types—size separation would not be required.

In some embodiments, amplified nucleic acids are detected by hybridization with a specific probe. Probe oligonucleotides, complementary to a portion of the amplified target sequence may be used to detect amplified fragments. Hybridization may be detected in real time or in non-real time. Amplified nucleic acids for each of the target sequences may be detected simultaneously (i.e., in the same reaction vessel) or individually (i.e., in separate reaction vessels). In preferred embodiments, the amplified DNA is detected simultaneously, using two or more distinguishably-labeled, gene-specific oligonucleotide probes, one which hybridizes to the first target sequence, one which hybridizes to the second target sequence, and so forth.

The probe may be detectably labeled by methods known in the art. Useful labels include, e.g., fluorescent dyes (e.g., Cy5®, Cy3®, FITC, rhodamine, lanthamide phosphors, Texas red, FAM, JOE, Cal Fluor Red 610®, Quasar 670®), $^{32}$P, $^{35}$S, $^{3}$H, $^{14}$C, $^{125}$I, $^{131}$I, electron-dense reagents (e.g., gold), enzymes, e.g., as commonly used in an ELISA (e.g., horseradish peroxidase, beta-galactosidase, luciferase, alkaline phosphatase), colorimetric labels (e.g., colloidal gold), magnetic labels (e.g., Dynabeads™), biotin, dioxigenin, or haptens and proteins for which antisera or monoclonal antibodies are available. Other labels include ligands or oligonucleotides capable of forming a complex with the corresponding receptor or oligonucleotide complement, respectively. The label can be directly incorporated into the nucleic acid to be detected, or it can be attached to a probe (e.g., an oligonucleotide) or antibody that hybridizes or binds to the nucleic acid to be detected.

One general method for real time PCR uses fluorescent probes such as the TaqMan® probes, molecular beacons, and Scorpions. Real-time PCR quantitates the initial amount of the template with more specificity, sensitivity and reproducibility, than other forms of quantitative PCR, which detect the amount of final amplified product. Real-time PCR does not detect the size of the amplicon. The probes employed in Scorpion and TaqMan® technologies are based on the principle of fluorescence quenching and involve a donor fluorophore and a quenching moiety.

In a preferred embodiment, the detectable label is a fluorophore. The term "fluorophore" as used herein refers to a molecule that absorbs light at a particular wavelength (excitation frequency) and subsequently emits light of a longer wavelength (emission frequency). The term "donor fluorophore" as used herein means a fluorophore that, when in close proximity to a quencher moiety, donates or transfers emission energy to the quencher. As a result of donating energy to the quencher moiety, the donor fluorophore will itself emit less light at a particular emission frequency than it would have in the absence of a closely positioned quencher moiety.

The term "quencher moiety" as used herein means a molecule that, in close proximity to a donor fluorophore, takes up emission energy generated by the donor and either dissipates the energy as heat or emits light of a longer wavelength than the emission wavelength of the donor. In the latter case, the quencher is considered to be an acceptor fluorophore. The quenching moiety can act via proximal (i.e., collisional) quenching or by Förster or fluorescence resonance energy transfer ("FRET"). Quenching by FRET is generally used in TaqMan® probes while proximal quenching is used in molecular beacon and Scorpion type probes.

In proximal quenching (a.k.a. "contact" or "collisional" quenching), the donor is in close proximity to the quencher moiety such that energy of the donor is transferred to the quencher, which dissipates the energy as heat as opposed to a fluorescence emission. In FRET quenching, the donor fluorophore transfers its energy to a quencher which releases the energy as fluorescence at a longer wavelength. Proximal quenching requires very close positioning of the donor and quencher moiety, while FRET quenching, also distance related, occurs over a greater distance (generally 1-10 nm, the energy transfer depending on R-6, where R is the distance between the donor and the acceptor). Thus, when FRET quenching is involved, the quenching moiety is an acceptor fluorophore that has an excitation frequency spectrum that overlaps with the donor emission frequency spectrum. When quenching by FRET is employed, the assay may detect an increase in donor fluorophore fluorescence resulting from increased distance between the donor and the quencher (acceptor fluorophore) or a decrease in acceptor fluorophore emission resulting from decreased distance between the donor and the quencher (acceptor fluorophore).

Suitable fluorescent moieties include the following fluorophores known in the art: 4-acetamido-4'-isothiocyanatostilbene-2,2'disulfonic acid, acridine and derivatives (acridine, acridine isothiocyanate) Alexa Fluor® 350, Alexa Fluor® 488, Alexa Fluor® 546, Alexa Fluor® 555, Alexa Fluor® 568, Alexa Fluor® 594, Alexa Fluor® 647 (Molecular Probes), 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Black Hole Quencher™ (BHQ™) dyes (biosearch Technologies), BODIPY® R-6G, BOPIPY® 530/550, BODIPY® FL, Brilliant Yellow, coumarin and derivatives (coumarin, 7-amino-4-methylcoumarin (AMC, Coumarin 120), 7-amino-4-trifluoromethylcouluarin (Coumarin 151)), Cy2®, Cy3®, Cy3.5®, Cy5®, Cy5.5®, cyanosine, 4',6-diaminidino-2-phenylindole (DAP1), 5',5"-dibromopyrogallol-sulfonephthalein (Bromopyrogallol Red), 7-diethylamino-3-(4'-isothiocyanatophenyl)-4-methylcoumarin, diethylenetriamine pentaacetate, 4,4'-diisothiocyanatodihydro-stilbene-2,2'-disulfonic acid, 4,4'-diisothiocyanatostilbene-2,2'-disulfonic acid, 5-[dimethylamino]naphthalene-1-sulfonyl chloride (DNS, dansyl chloride), 4-(4'-dimethylaminophenylazo)benzoic acid (DABCYL), 4-dimethylaminophenylazophenyl-4'-isothiocyanate (DABITC), Eclipse™ (Epoch Biosciences Inc.), eosin and derivatives (eosin, eosin isothiocyanate), erythrosin and derivatives (erythrosin B, erythrosin isothiocyanate), ethidium, fluorescein and derivatives (5-carboxyfluorescein (FAM), 5-(4,6-dichlorotriazin-2-yl)aminofluorescein (DTAF), 2',7'-dimethoxy-4'5'-dichloro-6-carboxyfluorescein (JOE), fluorescein, fluorescein isothiocyanate (FITC), hexachloro-6-carboxyfluorescein (HEX), QFITC (XRITC), tetrachlorofluorescein (TET)), fluorescamine, IR144, IR1446, Malachite Green isothiocyanate, 4-methylumbelliferone, ortho cresolphthalein, nitrotyrosine, pararosaniline, Phenol Red, B-phycoerythrin, R-phycoerythrin, o-phthaldialdehyde, Oregon Green®, propidium iodide, pyrene and derivatives (pyrene, pyrene butyrate, succinimidyl 1-pyrene butyrate), QSY® 7, QSY® 9, QSY® 21, QSY® 35 (Molecular Probes), Reactive Red 4 (Cibacron® Brilliant Red 3B-A), rhodamine and derivatives (6-carboxy-X-rhodamine (ROX), 6-carboxyrhodamine (R6G), lissamine rhodamine B sulfonyl chloride, rhodamine (Rhod), rhodamine B, rhodamine 123, rhodamine green, rhodamine X isothiocyanate, sulforhodamine B, sulforhodamine 101, sulfonyl chloride derivative of sulforhodamine 101 (Texas Red)), N,N,N',N'-tetramethyl-6-carboxyrhodamine (TAMRA), tetramethyl rhodamine, tetramethyl rhodamine isothiocyanate (TRITC), riboflavin, rosolic acid, terbium chelate derivatives.

Other fluorescent nucleotide analogs can be used, see, e.g., Jameson, 278 *Meth. Enzymol,* 363-390 (1997); Zhu, 22 *Nucl. Acids Res.* 3418-3422 (1994). U.S. Pat. Nos. 5,652,099 and 6,268,132 also describe nucleoside analogs for incorporation into nucleic acids, e.g., DNA and/or RNA, or oligonucleotides, via either enzymatic or chemical synthesis to produce fluorescent oligonucleotides. U.S. Pat. No. 5,135,717 describes phthalocyanine and tetrabenztriazaporphyrin reagents for use as fluorescent labels.

Suitable quenchers are selected based on the fluorescence spectrum of the particular fluorophore. Useful quenchers include, for example, the Black Hole™ quenchers BHQ-1, BHQ-2, and BHQ-3 (Biosearch Technologies, Inc.) and the ATTO-series of quenchers (ATTO 540Q, ATTO 580Q, and ATTO 612Q; Atto-Tec GmbH).

The detectable label can be incorporated into, associated with or conjugated to a nucleic acid. The label can be attached by spacer arms of various lengths to reduce potential steric hindrance or impact on other useful or desired properties. See, e.g., Mansfield, 9 *Mol. Cell.* Probes 145-156 (1995). Detectable labels can be incorporated into nucleic acids by covalent or non-covalent means, e.g., by transcription, such as by random-primer labeling using Klenow polymerase, or nick translation, or amplification, or equivalent as is known in the art. For example, a nucleotide base is conjugated to a detectable moiety, such as a fluorescent dye, and then incorporated into nucleic acids during nucleic acid synthesis or amplification. In one embodiment, the pathogens are detected in 3 channels.

With Scorpion detection systems, sequence-specific priming and PCR product detection is achieved using a single molecule. The Scorpion probe maintains a stem-loop configuration in the unhybridized state. The fluorophore is quenched by a moiety coupled to the 5' end, although in suitable embodiments, the fluorophore is attached to the 5' end and is quenched by a moiety coupled to the 3' end. The 3' portion of the stem also contains a sequence that is complementary to the extension product of the primer. This sequence is linked to the 5' end of the Scorpion probe via a non-amplifiable monomer. After extension using the Scorpion primer, the specific probe sequence is able to bind to its complement within the extended amplicon thus opening up the hairpin loop. This prevents fluorescence from being quenched and a signal is observed. A specific target is amplified by the reverse primer and the primer portion of the Scorpion, resulting in an extension product. A fluorescent signal is generated due to the separation of the fluorophore from the quencher resulting from the binding of the probe element of the Scorpion to the extension product.

TaqMan® probes (Heid, et al., *Genome Res* 6: 986-994, 1996) use the fluorogenic 5' exonuclease activity of Taq polymerase to measure the amount of target sequences in cDNA samples. TaqMan® probes are oligonucleotides that contain a donor fluorophore usually at or near the 5' base, and a quenching moiety typically at or near the 3' base. The quencher moiety may be a dye such as TAMRA or may be a non-fluorescent molecule such as 4-(4-dimethylaminophenylazo)benzoic acid (DABCYL). See Tyagi, et al., 16 Nature Biotechnology 49-53 (1998). When irradiated, the excited fluorescent donor transfers energy to the nearby quenching moiety by FRET rather than fluorescing. Thus, the close proximity of the donor and quencher prevents emission of donor fluorescence while the probe is intact.

TaqMan® probes are designed to anneal to an internal region of a PCR product. When the polymerase (e.g., reverse transcriptase) replicates a template on which a TaqMan® probe is bound, its 5' exonuclease activity cleaves the probe. This ends the activity of the quencher (no FRET) and the donor fluorophore starts to emit fluorescence which increases in each cycle proportional to the rate of probe cleavage. Accumulation of PCR product is detected by monitoring the increase in fluorescence of the reporter dye (note that primers are not labeled). If the quencher is an acceptor fluorophore, then accumulation of PCR product can be detected by monitoring the decrease in fluorescence of the acceptor fluorophore.

In a suitable embodiment, real time PCR is performed using any suitable instrument capable of detecting fluorescence from one or more fluorescent labels. For example, real time detection on the instrument (e.g. a ABI Prism® 7900HT sequence detector) monitors fluorescence and calculates the measure of reporter signal, or Rn value, during each PCR cycle. The threshold cycle, or Ct value, is the cycle at which fluorescence intersects the threshold value. The threshold value is determined by the sequence detection system software or manually.

In one embodiment, the detection of the target nucleic acids can be accomplished by means of so called Invader™ technology (available from Third Wave Technologies Inc. Madison, Wis.). In this assay, a specific upstream "invader" oligonucleotide and a partially overlapping downstream probe together form a specific structure when bound to complementary DNA template. This structure is recognized and cut at a specific site by the Cleavase enzyme, and this results in the release of the 5' flap of the probe oligonucleotide. This fragment then serves as the "invader" oligonucleotide with respect to synthetic secondary targets and secondary fluorescently labeled signal probes contained in the reaction mixture. This results in specific cleavage of the secondary signal probes by the Cleavase enzyme. Fluorescence signal is generated when this secondary probe, labeled with dye molecules capable of FRET, is cleaved. Cleavases have stringent requirements relative to the structure formed by the overlapping DNA sequences or flaps and can, therefore, be used to specifically detect single base pair mismatches immediately upstream of the cleavage site on the downstream DNA strand. See Ryan D et al. *Molecular Diagnosis* 4(2):135-144 (1999) and Lyamichev V et al. *Nature Biotechnology* 17:292-296 (1999), see also U.S. Pat. Nos. 5,846,717 and 6,001,567.

In some embodiments, melting curve analysis may be used to detect an amplification product. One advantage is the possible use of fewer dyes if desired. Melting curve analysis involves determining the melting temperature of a nucleic acid amplicon by exposing the amplicon to a temperature gradient and observing a detectable signal from a fluorophore. Melting curve analysis is based on the fact that a nucleic acid sequence melts at a characteristic temperature called the melting temperature ($T_m$), which is defined as the temperature at which half of the DNA duplexes have separated into single strands. The melting temperature of a DNA depends primarily upon its nucleotide composition. Thus, DNA molecules rich in G and C nucleotides have a higher $T_m$ than those having an abundance of A and T nucleotides.

Where a fluorescent dye is used to determine the melting temperature of a nucleic acid in the method, the fluorescent dye may emit a signal that can be distinguished from a signal emitted by any other of the different fluorescent dyes that are used to label the oligonucleotides. In some embodiments, the fluorescent dye for determining the melting temperature of a nucleic acid may be excited by different wavelength energy than any other of the different fluorescent dyes that are used to label the oligonucleotides. In some embodiments, the second fluorescent dye for determining the melting temperature of the detected nucleic acid is an intercalating agent. Suitable intercalating agents may include, but are not limited to SYBR™ Green 1 dye, SYBR™ dyes, Pico Green, SYTO dyes, SYTOX dyes, ethidium bromide, ethidium homodimer-1, ethidium homodimer-2, ethidium derivatives, acridine, acridine orange, acridine derivatives, ethidium-acridine heterodimer, ethidium monoazide, propidium iodide, cyanine monomers, 7-aminoactinomycin D, YOYO-1, TOTO-1, YOYO-3, TOTO-3, POPO-1, BOBO-1, POPO-3, BOBO-3, LOLO-1, JOJO-1, cyanine dimers, YO-PRO-1, TO-PRO-1, YO-PRO-3, TO-PRO-3, TO-PRO-5, PO-PRO-1, BO-PRO-1, PO-PRO-3, BO-PRO-3, LO-PRO-1, JO-PRO-1, and mixture thereof. In suitable embodiments, the selected intercalating agent is SYBR™ Green 1 dye.

By detecting the temperature at which the fluorescence signal is lost, the melting temperature can be determined. For example, amplified target nucleic acids may have a melting temperature that differs by at least about 1° C., more preferably by at least about 2° C., or even more preferably by at least about 4° C. from the melting temperature of any other amplified target nucleic acids. By observing differences in the melting temperature(s) of the gene or gene fragment targets from the respective amplification products, one can confirm the presence or absence of the pathogenic genes in the sample.

Detection of Influenza A and Influenza B

The presence of Influenza A and/or Influenza B in a patient may be determined by detecting an Influenza A and/or Influenza B target nucleic acid in a biological sample. Suitable target nucleic acids include, for example, the M gene (encompassing M1 and M2 for Influenza A, and M1 and BM2 for Influenza B) or fragments thereof. Nucleotide sequences of the M gene for Influenza A and Influenza B are provided at the GenBank Accession Numbers listed in Table 2. Sequences for Influenza A are shown in FIGS. 1, 2, and 3 (SEQ ID NOs: 1, 2, and 3). Sequences for Influenza B are shown in FIGS. 4, 5, and 6 (SEQ ID NOs: 4, 5, and 6). An equivalent M gene target nucleic acid sequence from any other Influenza A or Influenza B strain including for example, those listed in Table 2 may be used.

TABLE 2

M Gene Nucleotide Sequences from GenBank

| Target Gene Region | Accession Number | Nucleotides in M gene for each Accession Number Sequence |
|---|---|---|
| Flu A: M gene (including M1 and M2 or Matrix 1 and Matrix 2) | ay947478, cy003697, cy003770, cy002529, cy000122, cy001105, cy002505, cy002985, cy002353, cy002057 | 1-910, 1-1002, 1-1015, 1-1023, 1-1025, 1-1025, 1-1026, 1-1027, 1-1027, 1-1027 |
| Flu B: M gene (including M1 and BM2) | ay581982, ay581979, ay581980, ay581981, ay581972, dq508916, ay260955, ay260941 | 1-1076, 1-1076, 1-1076, 1-1076, 1-1079, 1-1155, 1-1171, 1-1180 |
| RSV A: M gene (nucleotides 3224-4180) | u39662, u39661, u63644, u50363, u50362, m74568, af035006 | 3232-4002, 3224-4180, 3252-4209, 3252-4209, 3252-4209, 3252-4209, 3253-4210 |
| RSV B: M gene | af013255, nc_001781, af013254, ay353550 | 3263-4033, 3263-4033, 3263-4033, 3261-4031 |

In preferred embodiments, the target nucleic acid corresponds to nucleotides 1-1027 of the M gene or a fragment thereof for Influenza A. In particularly preferred embodiments, the target nucleic acid, to which an oligonucleotide is to be directed, is SEQ ID NO: 32, as shown below.

```
                                          SEQ ID NO: 32
 1  TCACCTCTGA CTAAGGGGAT TTTRGGRTTT GTGTTCACGC
    TCACCGTGCC

51  CAGTGAGCGR GGACTGCARC GTAGACGCTT TGTCCAAAAT
    GC
```

The full target sequence of SEQ ID NO: 32, or any portion thereof, may be amplified and detected using any appropriate primers and probes. Although any suitable region within the Flu A target sequence may be amplified and detected as an indicator of the presence of Flu A, particularly useful primers include, for example, those directed to SEQ ID NO: 13 and SEQ ID NO: 14 of the M gene, or complements thereof (underlined in SEQ ID NO: 32). One useful probe, italicized and bolded in SEQ ID NO: 32, is directed to SEQ ID NO: 15 of the M gene.

In preferred embodiments, the target nucleic acid corresponds to nucleotides 1-1076 of the M gene or a fragment thereof for Influenza B. In particularly preferred embodiments, the target nucleic acid, to which an oligonucleotide is to be directed, is SEQ ID NO: 33, as shown below.

```
                                          SEQ ID NO: 33
 1 C AGAAGAGCTG CAAAGCAACA TTGGAGTATT GAGATCTCTT
   GGAGCAAGTC
```

-continued

```
 51 AAAAGAATGG GGAAGGAATT
    GCAAAGGATG TAATGGAAGT GCTAAAGCAG

101 AGCTCCATGG GAAATTCAGC
```

The full target sequence of SEQ ID NO: 33, or any portion thereof, may be amplified and detected using any appropriate primers and probes. Although any suitable region within the Flu B target sequence may be amplified and detected as an indicator of the presence of Flu B, particularly useful primers include, for example, those directed to SEQ ID NO: 17 and SEQ ID NO: 18 of the M gene, or complements thereof (underlined in SEQ ID NO: 33). One useful probe, italicized and bolded in SEQ ID NO: 33, is directed to SEQ ID NO: 19 of the M gene.

Detection of Respiratory Syncytial Virus A and Respiratory Syncytial Virus B

The presence of RSV A and/or RSV B in a patient may be determined by detecting an RSV A and/or RSV B target nucleic acid in a biological sample. Suitable target nucleic acids include, for example, the M gene or fragments thereof. Nucleotide sequences of the M gene for RSV A and RSV B are provided at the GenBank Accession Numbers listed in Table 2. Sequences for RSV A are shown in FIGS. 7, 8, and 9 (SEQ ID NOs: 7, 8, and 9). Sequences for RSV B are shown in FIGS. 10, 11, and 12 (SEQ ID NOs: 10, 11, and 12). An equivalent M gene target nucleic acid sequence from any other RSV A or RSV B strain including for example, those listed in Table 2 may be used.

In preferred embodiments, the target nucleic acid corresponds to nucleotides 3252-4209 of the M gene or a fragment thereof for RSV A. In particularly preferred embodiments, the target nucleic acid, to which an oligonucleotide is to be directed, is SEQ ID NO: 34, as shown below.

```
                                             SEQ ID NO: 34
  1 CACGAAGGCT CCACATACAC AGCTGCTGTT CAATACAATG
    TCTTAGAAAA

51 AGACGATGAC CCTGCATCAC TTACAATATG GGTGCCCATG
    TTCCAATCAT

101 CYATGCCAGC AGATTTACTT ATAAAAGAAC TAGCTAATGT
    CAACATACTA

151 GTGAAACAAA TATCCACACC CAAKGGACCT TCAYTAAGAG
    TCATGATAAA

201 CTCAAGAAGT GCA
```

The full target sequence of SEQ ID NO: 34, or any portion thereof, may be amplified and detected using any appropriate primers and probes. Although any suitable region within the RSV A target sequence may be amplified and detected as an indicator of the presence of RSV A, particularly useful primers include, for example, those directed to SEQ ID NO: 21 and SEQ ID NO: 22 of the M gene, or complements thereof (underlined in SEQ ID NO: 34). One useful probe, italicized and bolded in SEQ ID NO: 34, is directed to SEQ ID NO: 23 of the M gene.

In preferred embodiments, the target nucleic acid corresponds to nucleotides 3263-4033 of the M gene or a fragment thereof for RSV B. In particularly preferred embodiments, the target nucleic acid, to which an oligonucleotide is to be directed, is SEQ ID NO: 35, as shown below.

```
                                             SEQ ID NO: 35
  1 CACGAAGGCT CCACATACAC AGCAGCTGTT CAGTACAATG
    TTCTAGAAAA

51 AGATGATGAT CCTGCATCAC TAACAATATG
    GGTGCCTATGTTCCAGTCAT

101 CTGTRCCAGCAGACTTGCTC ATAAAAGAAC TTGCAAGC
```

The full target sequence of SEQ ID NO: 35, or any portion thereof, may be amplified and detected using any appropriate primers and probes. Although any suitable region within the RSV B target sequence may be amplified and detected as an indicator of the presence of RSV B, particularly useful primers include, for example, those directed to SEQ ID NO: 25 and SEQ ID NO: 26 of the M gene, or complements thereof (underlined in SEQ ID NO: 35). One useful probe, italicized and bolded in SEQ ID NO: 35, is directed to SEQ ID NO: 27 of the M gene.

Preparation of an Internal Control

As a quality control measure, an internal amplification control (IC) may be included in one or more samples to be extracted and amplified. The skilled artisan will understand that any detectable sequence that is not derived from Flu A, Flu B, RSV A, or RSV B probes can be used as the control sequence. These controls can be mixed with the sample (or with purified nucleic acids isolated from the sample), and amplified with sample nucleic acids using a pair complementary to the control sequence. If PCR amplification is successful, the internal amplification control amplicons can then be detected and differentiated from Flu A, Flu B, RSV A, and RSV B amplicons using a probe to the control sequence. Additionally, if included in the sample prior to purification of nucleic acids, the control sequences can also act as a positive purification control.

All publications, patent applications, issued patents, and other documents referred to in the present disclosure are herein incorporated by reference as if each individual publication, patent application, issued patent, or other document were specifically and individually indicated to be incorporated by reference in its entirety. Definitions that are contained in text incorporated by reference are excluded to the extent that they contradict definitions in this disclosure.

EXAMPLES

The present invention is further illustrated by the following examples, which should not be construed as limiting in any way.

Example 1: Materials and Methods

In accordance with the methods of the present invention, viral pathogens were detected in biological samples following the procedures described in this example. Using methods similar to the ones described below, it would be possible for the skilled artisan to alter the parameters for the detection of additional target nucleic acids or use alternate probe/primer designs to the ones shown herein.

The diagnostic panel in this example was designed to detect any of Influenza A, Influenza B, RSV A, or RSV B DNA in a singleplex or multiplex reaction. Specifically, it was designed to detect the M gene of each pathogen. The assay includes reagents and primers for the detection of nucleic acid from the target sequence of Flu A, Flu B, RSV A, and RSV B. The assay may further include an internal control (IC) to verify adequate processing of the target viruses and to monitor the presence of inhibition in the amplification assay to avoid false negative results.

The diagnostic test involved a two-step procedure: (1) the extraction of nucleic acid from, for example, the subject's nasal cavity for use as the testing template and (2) one-step RT-PCR using reverse transcription to convert target RNA to cDNA followed by the amplification and detection of the target template(s).

Materials

Nucleic acid extraction was performed using QIAamp viral RNA Mini Kit (Qiagen). Reverse transcription was carried out with the ImProm-II Reverse Transcription System and RNasin Plus RNase Inhibitor (Promega). Real-time PCR amplification utilized Scorpion Detection Technology (DxS Ltd) and FastStart DNA polymerase (Hoffman-La Roche).

The diagnostic test used a master mix containing enzymes, buffers, and dNTPs assembled according to Table 3.

TABLE 3

Master Mix Composition

| Component | Master Mix Concentration | Final Reaction Concentration |
|---|---|---|
| Tris-HCl, pH 8.3 @ 25° C. | 100.0 mM | 50.0 mM |
| MgCl$_2$ | 5.0 mM | 2.5 mM |
| KCl | 20.0 mM | 10.0 mM |
| EDTA | NA | NA |
| DTT | NA | NA |
| Tween20 | NA | NA |
| (NH$_4$)$_2$SO$_4$ | 10.0 mM | 5.0 mM |
| Glycerol | NA | NA |
| dNTPs (U, A, G, C) | 400.0 uM each | 200.0 uM each |
| FastStart DNA Polymerase (Roche) | 7.0 U | 3.5 U |

The diagnostic test used a primer mix having dye-labeled Scorpion primers and reverse primers. The Scorpion primers and reverse primers were specific for each of the targets being detected, as well as for the IC template. Accordingly, the primer mix contained the following primers: a Scorpion primer for Flu A, a Scorpion primer for Flu B, a Scorpion primer for RSV A, a Scorpion primer for RSV B, a Scorpion primer for IC a reverse primer for Flu A, a reverse primer for Flu B, a reverse primer for RSV A, a reverse primer for RSV B, and a reverse primer for IC. A summary of the targets and detectable labels associated with each Scorpion primer is shown in Table 4. A summary of the targets for the reverse primers is shown in Table 5. The concentration of the Scorpions was RSV A (300 nM), RSV B (300 nM), Flu A (300 nM), Flu B (300 nM), IC (150 nM). The concentration of the reverse primers was RSV (300 nM), Flu A (300 nM), Flu B (300 nM), IC (150 nM).

TABLE 4

Labeled Scorpion Primers

| Virus | Scorpion SEQ ID NO: | Fluorophore | Excitation | Emission | Target Gene |
|---|---|---|---|---|---|
| Flu A | 15 | JOE | 520 nm | 548 nm | M gene |
| Flu B | 19 | CAL Fluor Red 610 | 590 nm | 610 nm | M gene |
| RSV A | 23 | FAM | 495 nm | 520 nm | M gene |
| RSV B | 27 | FAM | 495 nm | 520 nm | M gene |
| IC | 31 | Quasar 670 (Q670) | 647 nm | 667 nm | IC RNA |

TABLE 5

Reverse Primers

| Reverse Primer | SEQ ID NO: | Target | Size |
|---|---|---|---|
| Flu A | 14 | M gene | 19mer |
| Flu B | 18 | M gene | 21mer |
| RSV A | 22 | M gene | 21mer |
| RSV B | 26 | M gene | 21mer |
| IC | 30 | Synthetic DNA | 18 bp |

An IC fragment (armored RNA)—was included in each reaction to verify the success of the extraction procedure, monitor the quality of the amplification reaction, and detect the presence of any amplification inhibitors. The IC is a Armored RNA fragment with a predetermined sequence cloned into a carrier vector. It was spiked into each specimen before nucleic acid extraction. The IC sequence is provided below as SEQ ID NO: 36.

```
                                                   SEQ ID NO: 36
  1 TGTGATGGAT ATCTGCAGAA TTCGCCCTTT GTTTCGACCT AGCTTGCCAG TTCGCAGAAT

51 TTGTTGCTCG TCAGTCGTCG GCGGTTTTAA GGGCGAATTC CAGCACACTG GCGGCCGTTA
```

Furthermore, two positive controls (PC1 and PC2) reactions were run in separate reaction wells. PC1 is an Armored RNA particle containing the target region for RSV A and Flu A. The PC1 sequence is provide below as SEQ ID NO:37

```
                                                   SEQ ID NO: 37
   1  GCATGCGCAT TTTGGACAAA GCGTCTACGC TGCAGTCCCC
      GCTCACTGGG

50  CACGGTGAGC GTGAACACAA ATCCTAAAAT CCCCTTAGTC
      AGAGGTGAGG

100  ATCCTGCACT TCTTGAGTTT ATCATGACTC TTAGTGAAGG
      TCCCTTGGGT

150  GTGGATATTT GTTTCACTAG TATGTTGACA TTAGCTAGTT
      CTTTTATAAG
```

-continued

```
200  TAAATCTGCT GGCATAGATG ATTGGAACAT GGGCACCCAT
     ATTGTAAGTG

250  ATGCAGGGTC ATCGTCTTTT TCTAGGACAT TGTATTGAAC
     AGCAGCTGTG

300  TATGTGGAGC CTTCGTGGGT ACC
```

PC2 is an Armored RNA particle containing the target region for RSV B and Flu B. The PC2 sequence is provided below as SEQ ID NO: 38

```
                                              SEQ ID NO: 38
1    GCATGCAGAG CTGAATTTCC CATAGAGCTC TGTTTTAGCA
     CTTCCATTAC

50   ATCTTTGGCA ATTCCTTCTC CATTCTTTTG ACTTGCTCCT
     AGAGATCTCA

100  ACACTCCAAT GTTGCTTTGC AGCTGGATCC GCTTGCAAGT
     TCTTTTATGA

150  GCAAGTCTGC TGGTACAGAT GACTGGAACA TAGGCACCCA
     TATTGTTAGT

200  GATGCAGGAT CATCATCTTT TTCTAGAACA TTGTACTGAA
     CAGCTGCTGT

250  GTATGTGGAG CCTTCGTGGG TACC
```

Armored PC1, PC2 and IC were constructed by Armored RNA technology (Asuragen, Tex.).

The amplification reaction was prepared according to Table 6.

TABLE 6

Amplification Reaction Mixture

| Component | Volume (μL) |
| --- | --- |
| Fast Start Master Mix | 12.5 |
| Primer Mix | 2.5 |
| ImProm-II ™ Reverse Transcriptase (Promega, Madison, WI) | 0.5 |
| RNasin ® Plus RNase Inhibitor (Promega, Madison WI) | 0.5 |
| Patient Sample or Control | 5.0 |
| Water | 4.0 |

Specimen Collection, Preparation, and Handling

Nasopharyngeal swabs in liquid viral transport media or nasopharyngeal washes was collected in a sterile container. Specimens were stored at 2° C.-8° C. or −20° C. until testing. Immediately before sample preparation, specimens were equilibrated to room temperature (15-25° C.). Next, 5 μl of the IC RNA at 300 copies/ul was spiked into 135 μL of each specimen. Nucleic acids were extracted using the QIAamp® Viral RNA Mini Kit (Cat. No. 52905, Qiagen, Valencia, Calif.). Extraction was according to the manufacturer's instructions except that the final elution used 40 μL of buffer AVE instead of the 200 μL recommended by the manufacturer. Nucleic acid samples were stored at −20° C., if not assayed immediately.

Nucleic Acid Amplification and Detection

The amplification reaction was performed using Applied BioSystems 7500 Real-Time PCR Detection System with the following channel, dye, and analyte sets: Channel A: FAM for RSV; Channel B: JOE for Flu A; Channel D: CFR610 for Flu B; Channel E: Q670 for IC; Calibration dye: none. The cycling parameters were as follows: 47° C. for 30 minutes (reverse transcription); 95° C. for 10 minutes (hot start activation), and 50 cycles of 95° C. for 15 seconds, 60° C. for 45 seconds (data collection). Following the run, the cutoffs were determined as in Table 7 below.

TABLE 7

Fluorescence Threshold and Cutoff Values

| Analyte | Channel | Threshold (ΔRn) | Positive cutoff (Ct) | Equivocal zone (Ct) | Negative cutoff (Ct) |
| --- | --- | --- | --- | --- | --- |
| Flu A | JOE | 30,000 | <40 | 40.1-44.9 | >45 |
| Flu B | CRF 610 | 30,000 | <40 | 40.1-44.9 | >45 |
| RSV | FAM | 30,000 | <40 | 40.1-44.9 | >45 |
| IC | Q670 | 12,500 | <40 | NA | NA |
| Analyte | Channel | Threshold (ΔRn) | Positive cutoff (Ct) | Equivocal zone (Ct) | Negative cutoff (Ct) |

Interpretation of Test Results

The Negative Control was the primary specimen matrix free of the target being detected or water. To verify the validity of the run, the negative control well was reported as follows: FAM: Not detected; JOE: Not detected; CFR610: Not detected; Q670: Detected. If these results were not found, then the entire plate was interpreted as failed and was retested.

The Positive Controls 1 and 2 (PC1 and PC2) contained an Armored RNA particle possessing the target regions. To verify the validity of the run, the PC1 was confirmed to be: FAM: Detected; JOE: Detected; CFR610: Not Detected; Q670: Not Detected and PC2 was confirmed to be: FAM: Detected; JOE: Not Detected; CFR610: Detected; Q670: Not Detected. If these results were not found, then the entire plate was interpreted as failed, and was retested.

The data was collected and patient samples analyzed for the presence of one or more pathogenic species. Patient samples having a positive result for any one or more of the pathogenic species were scored as positive for those species. Patient samples having a negative result for all pathogenic species were only scored as negative provided that the internal control target nucleic acid was detected and the positive control sample assay was positive for Flu A, Flu B, RSV A, and RSV B target nucleic acids.

Results from these tests may be correlated with the clinical history, epidemiological data, and other data available to the attending physician in evaluating the patient. As with other diagnostic tests, negative results do not rule out the diagnosis of Influenza and RSV infections by Flu A, Flu B, RSV A, or RSV B. For example, false negatives may occur when the infecting virus has genomic mutations, insertions, deletions, or rearrangements. Furthermore, false positive results may occur. Repeat testing or testing with a different device may be indicated in some settings, e.g. patients with a low likelihood of Influenza and RSV infection by Flu A, Flu B, RSV A, or RSV B.

Individual samples were interpreted based on the matrix shown in Table 8.

TABLE 8

Interpretation of Results

| Assay Result Reported | | | | |
|---|---|---|---|---|
| FAM or equivalent | Joe or equivalent | CFR610 or equivalent | Q670 or equivalent (Internal Control) | Interpretation of Result |
| Detected | Not Detected | Not Detected | NA* | FAM or equivalent target detected |
| Not Detected | Detected | Not Detected | NA* | Joe or equivalent target detected |
| Not Detected | Not Detected | Detected | NA* | CFR610 or equivalent target detected |
| Detected | Detected | Not Detected | NA* | Both FAM or equivalent and Joe or equivalent targets detected |
| Detected | Not Detected | Detected | NA* | Both FAM or equivalent and CFR610 or equivalent targets detected |
| Not Detected | Detected | Detected | NA* | Both Joe or equivalent and CFR610 or equivalent targets detected |
| Not Detected | Not Detected | Not Detected | Detected | Neither target detected |
| Not Detected | Not Detected | Not Detected | Not Detected | Test Invalid |

NA = not applicable*. Detection of the Internal Control is not required for a positive result.

Example 2: Confirmation of Multiplex PCR Assay Results

The samples were either actual clinical specimens obtained from patients or contrived samples that were prepared from pathogen-negative biological material and spiked with the indicated respiratory virus.

The multiplex assay was compared to other detection assays. The sensitivity and specificity of the detection methods of the invention were investigated. Specimens were extracted and amplification was performed as described in Example 1. Pro-Flu 1 and Singleplex TaqMan® assays for RSV, Flu A and Flu B were used for comparison.

In one study, a total of 109 nasal wash patient samples were prepared and tested for Flu A, Flu B, and RSV. Extracted samples were tested via Simplexa™ Flu/RSV assay and Prodesse ProFlu-1 Assay. Any discrepant results were further tested by a referee singleplex TaqMan assay. One RSV positive sample by both assays was also detected as Flu A co-infection by Simplexa but ProFlu-1 detected the sample only as a RSV positive sample. Singleplex RSV and Flu A TaqMan assay revealed that it was positive both for RSV and Flu A.

In a separate validation assay, 3 RSV/Flu negative clinical samples were spiked with different concentrations of RSV, Flu A or Flu B and tested using both TaqMan and Simplexa™ assays. All assays reported positive controls except the Flu B TaqMan assay which was invalid due to its failure to detect the Flu B positive control The Simplexa™ Respiratory-1 RSV vs. RSV singleplex TaqMan® concordance was verified with 16 clinical samples. Of the 16 samples run, 6 samples tested negative and consisted of 2 nasal washes, 1 nasal swab, 1 lesion, 1 BAL, and 1 BW. Ten RSV positive samples consisted of 8 nasal washes, 1 sputum, and 1 BAL. Two RSV discrepant samples tested positive in the Simplexa™ assay and negative in the TaqMan assay. No additional referee assay was used to corroborate the results, which are summarized in Table 9.

TABLE 9

Simplexa ™ vs. TaqMan Concordance RSV

| RSV | | TaqMan Singleplex | | | | | |
|---|---|---|---|---|---|---|---|
| | | Positive | Negative | Total | Sensitivity | Specificity | Concordance |
| Simplexa ™ Multiplex | Positive | 8 | 2 | 10 | 100% | | |
| | Negative | 0 | 6 | 6 | | 75% | |
| | Total | 8 | 8 | 16 | | | 87.50% |

Due to the limited number of Flu A and Flu B specimens, 16 contrived Flu A and 16 contrived Flu B samples were prepared by spiking pathogen-negative biological extracts from 16 clinical samples with either Flu A or Flu B. The spiked extracts were tested by TaqMan and Simplexa™ assays. All 16 spiked extracts for each pathogen tested positive for the respective pathogen in both assays. The results for Flu A are summarized in Table 10 and show the clinical samples tested before and after addition of Flu A. The Simplexa™ Respiratory-1 Flu B detected 16 spiked clinical samples. Flu B concordance was unavailable due to a failed TaqMan assay. The positive control performed as expected for all samples in the Simplexa™ assay.

TABLE 10

Simplexa™ vs. TaqMan Concordance Flu A

| Flu A | | TaqMan Singleplex | | | | | |
|---|---|---|---|---|---|---|---|
| | | Positive | Negative | Total | Sensitivity | Specificity | Concordance |
| Simplexa™ Multiplex | Positive | 16 | 0 | 16 | 100% | | |
| | Negative | 0 | 16 | 16 | | 100% | |
| | Total | 16 | 16 | 32 | | | 100% |

The above studies verified that the Simplexa™ assay performed equally well to, or better than, singleplex TaqMan® assay in Flu and RSV detection. As such, the methods of the present invention are useful in diagnostic assays for the detection of Flu and RSV viral pathogens.

Example 3: Cross-Reactivity of the Multiplex Flu and RSV Pathogen Assay

DNA was extracted from the organisms listed below and assayed in the multiplex PCR system described above. No cross-reactivity was measured for the following species:

Human genomic DNA, Parainfluenza 1, Parainfluenza 2, Parainfluenza 3, Rhinovirus, Coronavirus 229E, Coronavirus OC43, Coronavirus NL 63, Adenovirus, *Streptococcus pneumoniae*, *Chlamydophila pneumoniae*, and *Bordetella*.

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the invention claimed.

Thus, it should be understood that although the present invention has been specifically disclosed by preferred embodiments and optional features, modification, improvement, and variation of the inventions disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other embodiments are set forth within the following claims.

What is claimed is:

1. A multiplex PCR kit consisting essentially of:
   (a) is a primer pair comprising two of SEQ ID NO: 13, 14, or 15, or a full complement thereof and a first probe consisting of SEQ ID NO: 16 or 40, a sequence of 16-18 nucleotides and 90% identical to SEQ ID NO: 16 or 40, or a complement thereof that is 16-18 nucleotides long; and
   (b) is a primer pair comprising (i) SEQ ID NO: 17 or a full complement thereof, and (ii) SEQ ID NO: 18, or 19, or a full complement thereof, and a second probe consisting of SEQ ID NO: 20, a sequence of 21-25 nucleotides and 90% identical to SEQ ID NO: 20, or a complement thereof that is 21-25 nucleotides long; and at least one of
   (c) is a primer pair comprising two of SEQ ID NO: 21, 22, or 23, or a full complement thereof and a third probe consisting of SEQ ID NO: 24, a sequence of 19-23 nucleotides and 90% identical to SEQ ID NO: 24, or a complement thereof that is 19-23 nucleotides long; or
   (d) is a primer pair comprising two of SEQ ID NO: 25, 26, or 27, or a full complement thereof and a fourth probe consisting of SEQ ID NO: 28, a sequence of 28-34 nucleotides and 90% identical to SEQ ID NO: 28, or a complement thereof that is 28-34 nucleotides long;
   wherein the probes are attached to one or more detectable labels selected from the group consisting of fluorescent dyes, 32P, 35S, 3H, 14C, 125I, 131I, electron-dense reagents, enzymes, colorimetric labels, magnetic labels, biotin, dioxigenin, haptens, proteins for which antisera or monoclonal antibodies are available, and ligands capable of forming a complex with a corresponding receptor.

2. The kit of claim 1 consisting essentially of (a), (b), (c), and (d).

3. The kit of claim 1, wherein at least one of said primers suitable for amplifying said genes or fragments thereof is a Scorpion primer.

4. The kit of claim 1, wherein said kit consists essentially of at least one primer suitable for amplifying each of said genes or fragment thereof.

* * * * *

SEQUENCE LISTING

```
<160> NUMBER OF SEQ ID NOS: 40

<210> SEQ ID NO 1
<211> LENGTH: 1027
<212> TYPE: DNA
<213> ORGANISM: Influenza A virus

<400> SEQUENCE: 1
agcaaaagca ggtagatatt gaaagatgag ccttctaacc gaggtcgaaa cgtatgttct      60
ctctatcgtt ccatcaggcc ccctcaaagc cgaaatcgcg cagagacttg aagatgtctt     120
tgctgggaaa acacagatc ttgaggctct catggaatgg ctaaagacaa gaccaattct     180
gtcacctctg actaagggga ttttggggtt tgtgttcacg ctcaccgtgc ccagtgagcg     240
aggactgcag cgtagacgct ttgtccaaaa tgcccttaat gggaatgggg atccaaataa     300
catggacaaa gcagtcaaac tgtatagaaa acttaagagg gagataacat tccatggggc     360
caaagaaata gcactcagtt attctgctgg tgcacttgct agttgcatgg gcctcatata     420
```

```
caataggatg ggggctgtaa ccaccgaagt ggcatttggc ctggtatgtg caacatgtga    480
acagattgct gactcccagc acaggtctca taggcaaatg gtggcaacaa ccaatccatt    540
aataaaacat gagaacagaa tggttttggc cagcactaca gctaaagcta tggagcaaat    600
ggctggatca agtgagcagg cagcggaggc catggagatt gctagtcagg ccaggcaaat    660
ggtgcaggca atgagaaccg ttgggactca tcctagttcc agtactggtc taagagatga    720
tcttcttgaa aatttgcaga cctatcagaa acgaatggga gtacagatgc agcgattcaa    780
gtgacccgct tgttgttgct gcgagtatca ttgggatctt gcacttgata ttgtggattc    840
ttgatcgtct tttttcaaa tgcatctatc gactcttcaa acacgcctg aaagagggc      900 cttctacgga aggagtacct gagtctatga gggaagaata tcggaaggaa cagcagaatg    960
ctgtggatgc tgacgacagt cattttgtca gcatagagct ggagtaaaaa actaccttgt   1020
ttctact                                                             1027

<210> SEQ ID NO 2
<211> LENGTH: 1027
<212> TYPE: DNA
<213> ORGANISM: Influenza A virus

<400> SEQUENCE: 2
agcaaaagca ggtagatatt gaaagatgag tcttctaacc gaggtcgaaa cgtacgttct     60
ctctatcgtc ccgtcaggcc ccctcaaagc cgagatcgca cagagacttg aagatgtatt    120
tgctggaaag aataccgatc ttgaggctct catggagtgg ctaaagacaa gaccaatcct    180
gtcacctctg actaagggga ttttaggatt tgtgttcacg ctcaccgtgc ccagtgagcg    240
aggactgcaa cgtagacgct ttgtccaaaa tgcccttaat gggaatgggg atccaaataa    300
tatggacaga gcagtcaaac tgtatcgaaa gcttaagagg gagataacat ccatggggc     360 caaagaaata gcactcagtt attctgctgg tgcacttgcc agttgtatgg gactcatata    420
caacaggatg ggggctgtga ccaccgaatc agcatttggc cttatatgcg caacctgtga    480
acagattgcc gactcccagc ataagtctca taggcaaatg gtaacaacaa ccaatccatt    540
aataagacat gagaacagaa tggttctggc cagcactaca gctaaggcta tggagcaaat    600
ggctggatcg agtgaacaag cagctgaggc catggaggtt gctagtcagg ccaggcagat    660
ggtgcaggca atgagagcca ttgggactca tcctagctct agcactggtc tgaaaaatga    720
tctccttgaa aatttgcagg cctatcagaa acgaatgggg gtgcagatgc aacgattcaa    780
gtgatcctct tgttgttgcc gcaagtataa ttgggattgt gcacctgata ttgtggatta    840
ttgatcgcct ttttccaaa agcatttatc gtatctttaa acacggttta aaaagagggc    900
cttctacgga aggagtacca gagtctatga gggaagaata tcgggaggaa cagcagaatg    960
ctgtggatgc tgacgatggt cattttgtca gcatagagct agagtaaaaa actaccttgt   1020
ttctact                                                             1027

<210> SEQ ID NO 3
<211> LENGTH: 1027
<212> TYPE: DNA
<213> ORGANISM: Influenza A virus

<400> SEQUENCE: 3
agcaaaagca ggtagatatt gaaagatgag ccttctaacc gaggtcgaaa cgtatgttct     60
ctctatcgtt ccatcaggcc ccctcaaagc cgagatcgcg cagagacttg aggatgtctt    120
```

| | | |
|---|---|---|
| tgctgggaaa aacacagatc ttgaggctct catggaatgg ctaaagacaa gaccaattct | 180 | |
| gtcacctctg actaagggga ttttggggtt tgtgttcacg ctcaccgtgc ccagtgagcg | 240 | |
| aggactgcag cgtagacgct ttgtccaaaa tgccctcaat gggaatggag atccaaataa | 300 | |
| catggacaaa gcagttaaac tgtataggaa acttaagagg gagataacgt tccatggggc | 360 | |
| caaagaaata gctctcagtt attctgctgg tgcacttgcc agttgcatgg gcctcatata | 420 | |
| caatagaatg ggggctgtaa ccactgaagt ggcatttggc ctggtatgtg caacatgtga | 480 | |
| acagattgct gactcccagc acaggtctca taggcaaatg gtggcaacaa ccaatccatt | 540 | |
| aataaaacat gagaacagaa tggttttggc cagcactaca gctaaggcta tggagcaaat | 600 | |
| ggctgggtca agtgagcagg cagcggaggc catggaaatt gctagtcagg ccaggcgaat | 660 | |
| ggtgcaggca atgagagccg ttgggactca tcctagctcc agtactggtc taagagatga | 720 | |
| tcttcttgaa aatttgcaga cctatcagaa acgaatgggg gtgcagatgc aacgattcaa | 780 | |
| gtgacccgct tgttgttgcc gcgaatatca ttgggatctt gcacttgata ttgtggattc | 840 | |
| ttgatcgtct tttcttcaaa tgcgtctatc gactcttcaa acacggcctt aaaagaggcc | 900 | |
| cttctacgga aggagtacct gagtctatga gggaagaata tcgaaaggaa cagcagaatg | 960 | |
| ctgtggatgc tgacgacagt cattttgtca gcatagagtt ggagtaaaaa actaccttgt | 1020 | |
| ttctact | 1027 | |

<210> SEQ ID NO 4
<211> LENGTH: 1076
<212> TYPE: DNA
<213> ORGANISM: Influenza B virus

<400> SEQUENCE: 4

| | | |
|---|---|---|
| atgtcgctgt ttggagacac aattgcctac ctgctttcat tgacagaaga tggagaaggc | 60 | |
| aaagcagaac tagcagaaaa attacactgt tggtttggtg ggaaagaatt tgacttagac | 120 | |
| tctgccttgg aatggataaa aacaaaaga tgcttaactg atatacaaaa agcactaatt | 180 | |
| ggtgcctcta tctgcttttt aaaacccaaa gaccaggaaa gaaaagaag attcatcaca | 240 | |
| gagcccttat caggaatggg aacaacagca acaaaaaaga aaggcctgat tctggctgag | 300 | |
| agaaaaatga agatgtgtgt gagctttcat gaagcatttg aaatagcaga aggccatgaa | 360 | |
| agctcagcgc tactatactg tctcatggtc atgtacctga tcctggaaa ttattcaatg | 420 | |
| caagtaaaac taggaacgct ctgtgctttg tgcgagaaac aagcatcaca ttcacacagg | 480 | |
| gctcatagca gagcagcgag atcttcagtg cctggagtga cgagaaat gcagatggtc | 540 | |
| tcagctatga acacagcaaa acaatgaat ggaatgggaa aaggagaaga cgtccaaaag | 600 | |
| ctggcagaag agctgcaaag caacattgga gtgctgagat ctcttgggc aagtcaaaag | 660 | |
| aatggggaag gaattgcaaa ggatgtaatg gaagtgctaa agcagagctc tatgggaaat | 720 | |
| tcagctcttg tgaagaaata tctataatgc tcgaaccatt tcagattctt tcaatttgtt | 780 | |
| cttttatctt atcagctctc catttcatgg cttgacaat agggcatttg aatcaaataa | 840 | |
| aaagaggagt aaacatgaaa atacgaataa aaagtccaaa caaagagaca ataaacagag | 900 | |
| aggtatcaat tttgagacac agttaccaaa aagaaatcca ggccaaagaa acaatgaaga | 960 | |
| aagtactctc tgacaacatg gaggtattga gtgaccacat aataattgag gggctttctg | 1020 | |
| ccgaagagat aataaaatg ggtgaaacag ttttggagat agaagaattg cattaa | 1076 | |

<210> SEQ ID NO 5
<211> LENGTH: 1076

```
<212> TYPE: DNA
<213> ORGANISM: Influenza B virus

<400> SEQUENCE: 5
atgtcgctgt ttggagacac aattgcctac ctgctttcat tgacagaaga tggagaaggc    60
aaagcagaac tagcagaaaa attacactgt tggttcggtg ggaaagaatt tgacctggac   120
tctgccttgg aatggataaa aacaaaaga tgcttaactg atatacaaaa agcactaatt   180
ggtgcctcta tctgcttttt aaacccaaa gaccaggaaa gaaaagaag attcatcaca    240
gagcctctat caggaatggg aacaacagca acaaaaaaga aaggtctgat tctagctgag   300
agaaaaatga aagatgtgt gagctttcat gaagcatttg aaatagcaga aggccatgaa    360
agctcagcgc tactatactg tctcatggtc atgtacctga tcctggaaa ttattcaatg    420
caagtaaaac taggaacgct ctgtgctttg tgcgagaaac aagcatcaca ttcacacagg   480
gctcatagca gagcagcgag atcttcagtg cctggagtga gacgagaaat gcagatggtc   540
tcagctatga acacagcaaa acaatgaat ggaatgggaa aggagaaga cgtccaaaaa    600
ctggcagaag agctgcaaag caacattgga gtactgagat ctcttggggc aagtcaaaag   660
aatggagaag gaattgcaaa ggatgtaatg gaagtgctaa agcagagctc tatgggaaat   720
tcagctcttg tgaagaaata tctataatgc tcgaaccatt tcagattctt tcaatttgtt   780
cttttatctt atcagctctc catttcatgg cttggacaat agggcatttg aatcaaataa    840
aagaggagt aaacatgaaa atacgaataa aaagtccaaa caagagaca ataaacagag     900
aggtatcaat tttgagacac agttaccaaa aagaaatcca ggccaaagaa acaatgaagg   960
aggtactctc tgacaacatg gaggtattga gtgaccacat aataattgag gggctttctg  1020
ccgaagagat aataaaaatg ggtgaaacag ttttggagat agaagaattg cattaa       1076

<210> SEQ ID NO 6
<211> LENGTH: 1076
<212> TYPE: DNA
<213> ORGANISM: Influenza B virus

<400> SEQUENCE: 6
atgtcgctgt ttggagacac aattgcctac ctgctttcat tgacagaaga tggagaaggc    60
aaagcagaac tagcagaaaa attacactgt tggttcggtg ggaaagaatt tgacctagac   120
tctgccttgg aatggataaa aacaaaaga tgcttaactg atatacaaaa agcactaatt   180
ggtgcctcta tctgcttttt aaacccaaa gaccaggaaa gaaaagaag attcatcaca    240
gagcctctat caggaatggg aacaacagca acaaaaaaga aaggcctgat tctagctgag   300
agaaaaatga aagatgtgt gagctttcat gaagcatttg aaatagcaga aggccatgaa    360
agctcagcgc tactatactg tctcatggtc atgtacctga tcctggaaa ttattcaatg    420
caagtaaaac taggaacgct ctgtgctttg tgcgagaaac aagcatcaca ttcacacagg   480
gctcatagca gagcagcgag atcttcagtg cctggagtga gacgagaaat gcagatggtc   540
tcagctatga acacagcaaa acaatgaat ggaatgggaa aggagaaga cgtccaaaaa    600
ctggcagaag agctgcaaag caacattgga gtactgagat ctcttggggc aagtcaaaag   660
aatggagaag gaattgcaaa ggatgtaatg gaagtgctaa agcagagctc tatgggaaat   720
tcagctcttg tgaagaaata tctataatgc tcgaaccatt tcagattctt tcaatttgtt   780
cttttatctt atcagctctc catttcatgg cttggacaat agggcatttg aatcaaataa    840
aagaggagt aaacatgaaa atacgaataa aaagtccaaa caagagaca ataaacagag     900
```

| | |
|---|---|
| aggtatcaat tttgagacac agttaccaaa aagaaatcca ggccaaagaa acaatgaagg | 960 |
| aggtactctc tgacaacatg gaagtattga gtgaccacat aataattgag gggctttctg | 1020 |
| ccgaagagat aataaaaatg ggtgaaacag ttttggagat agaagaattg cattaa | 1076 |

<210> SEQ ID NO 7
<211> LENGTH: 1020
<212> TYPE: DNA
<213> ORGANISM: Human respiratory syncytial virus A

<400> SEQUENCE: 7

| | |
|---|---|
| aaggaaaggg tggggcaaat atggaaacat acgtgaacaa gcttcacgaa ggctccacat | 60 |
| acacagctgc tgttcaatac aatgtcttag aaaaagacga tgaccctgca tcacttacaa | 120 |
| tatgggtgcc catgttccaa tcatctatgc cagcagattt acttataaaa gaactagcta | 180 |
| atgtcaacat actagtgaaa caaatatcca cacccaaggg accttcacta agagtcatga | 240 |
| taaactcaag aagtgcagtg ctagcacaaa tgcccagcaa atttaccata tgcgctaatg | 300 |
| tgtccttgga tgaaagaagc aaactagcat atgatgtaac cacaccctgt gaaatcaagg | 360 |
| catgtagtct aacatgccta aaatcaaaaa atatgttgac tacagttaaa gatctcacta | 420 |
| tgaagacact caaccctaca catgatatta ttgctttatg tgaatttgaa aacatagtaa | 480 |
| catcaaaaaa agtcataata ccaacatacc taagatccat cagtgtcaga ataaagatc | 540 |
| tgaacacact tgaaaatata acaaccactg aattcaaaaa tgctatcaca aatgcaaaaa | 600 |
| tcatcccttta ctcaggatta ctattagtca tcacagtgac tgacaacaaa ggagcattca | 660 |
| aatacataaa gccacaaagt caattcatag tagatcttgg agcttaccta gaaaaagaaa | 720 |
| gtatatatta tgttaccaca aattggaagc acacagctac acgatttgca atcaaaccca | 780 |
| tggaagatta accttttttcc tctacatcag tgtgttaatt catacaaaact ttctacctac | 840 |
| attcttcact tcaccatcac aatcacaaac actctgtggt tcaaccaatc aaacaaaact | 900 |
| tatctgaagt cccagatcat cccaagtcat tgtttatcag atctagtact caaataagtt | 960 |
| aataaaaaat atacacatgg ggcaaataat cattggagga atccaactaa tcacaatat | 1020 |

<210> SEQ ID NO 8
<211> LENGTH: 1020
<212> TYPE: DNA
<213> ORGANISM: Human respiratory syncytial virus A

<400> SEQUENCE: 8

| | |
|---|---|
| aaggaaaggg tggggcaaat atggaaacat acgtgaacaa gcttcacgaa ggctccacat | 60 |
| acacagctgc tgttcaatac aatgtcttag aaaaagacga tgaccctgca tcacttacaa | 120 |
| tatgggtgcc catgttccaa tcatctatgc cagcagattt acttataaaa gaactagcta | 180 |
| atgtcaacat actagtgaaa caaatatcca cacccaaggg accttcacta agagtcatga | 240 |
| taaactcaag aagtgcagtg ctagcacaaa tgcccagcaa atttaccata tgcgctaatg | 300 |
| tgtccttgga tgaaagaagc aaactagcat atgatgtaac cacaccctgt gaaatcaagg | 360 |
| catgtagtct aacatgccta aaatcaaaaa atatgttgac tacagttaaa gatctcacta | 420 |
| tgaagacact caaccctaca catgatatta ttgctttatg tgaatttgaa aacatagtaa | 480 |
| catcaaaaaa agtcataata ccaacatacc taagatccat cagtgtcaga ataaagatc | 540 |
| tgaacacact tgaaaatata acaaccactg aattcaaaaa tgctatcaca aatgcaaaaa | 600 |
| tcatcccttta ctcaggatta ctattagtca tcacagtgac tgacaacaaa ggagcattca | 660 |
| aatacataaa gccacaaagt caattcatag tagatcttgg agcttaccta gaaaaagaaa | 720 |

| | |
|---|---|
| gtatatatta tgttaccaca aattggaagc acacagctac acgatttgca atcaaaccca | 780 |
| tggaagatta accttttttcc tctacatcag tgtgttaatt catacaaact ttctacctac | 840 |
| attcttcact tcaccatcac aatcacaaac actctgtggt tcaaccaatc aaacaaaact | 900 |
| tatctgaagt cccagatcat cccaagtcat tgtttatcag atctagtact caaataagtt | 960 |
| aataaaaaat atacacatgg ggcaaataat cattggagga atccaacta atcacaatat | 1020 |

<210> SEQ ID NO 9
<211> LENGTH: 1020
<212> TYPE: DNA
<213> ORGANISM: Human respiratory syncytial virus A

<400> SEQUENCE: 9

| | |
|---|---|
| aaggaaaggg tggggcaaat atggaaacat acgtgaacaa gcttcacgaa ggctccacat | 60 |
| acacagctgc tgttcaatac aatgtcttag aaaaagacga tgaccctgca tcacttacaa | 120 |
| tatgggtgcc catgttccaa tcatctatgc cagcagattt acttataaaa gaactagcta | 180 |
| atgtcaacat actagtgaaa caaatatcca cacccaaggg accttcacta agagtcatga | 240 |
| taaactcaag aagtgcagtg ctagcacaaa tgcccagcaa atttaccata tgcgctaatg | 300 |
| tgtccttgga tgaaagaagc aaactagcat atgatgtaac cacaccctgt gaaatcaagg | 360 |
| catgtagtct aacatgccta aaatcaaaaa atatgttgac tacagttaaa gatctcacta | 420 |
| tgaagacact caaccctaca catgatatta ttgctttatg tgaatttgaa acatagtaa | 480 |
| catcaaaaaa agtcataata ccaacatacc taagatccat cagtgtcaga ataaagatc | 540 |
| tgaacacact tgaaaatata caaccactg aattcaaaaa tgctatcaca aatgcaaaaa | 600 |
| tcatcccta ctcaggatta ctattagtca tcacagtgac tgacaacaaa ggagcattca | 660 |
| aatacataaa gccacaaagt caattcatag tagatcttgg agcttaccta gaaaaagaaa | 720 |
| gtatatatta tgttaccaca aattggaagc acacagctac acgatttgca atcaaaccca | 780 |
| tggaagatta accttttttcc tctacatcag tgtgttaatt catacaaact ttctacctac | 840 |
| attcttcact tcaccatcac aatcacaaac actctgtggt tcaaccaatc aaacaaaact | 900 |
| tatctgaagt cccagatcat cccaagtcat tgtttatcag atctagtact caaataagtt | 960 |
| aataaaaaat atacacatgg ggcaaataat cattggagga atccaacta atcacaatat | 1020 |

<210> SEQ ID NO 10
<211> LENGTH: 840
<212> TYPE: DNA
<213> ORGANISM: Human respiratory syncytial virus B

<400> SEQUENCE: 10

| | |
|---|---|
| aaaagaacaa gatggggcaa atatggaaac atacgtgaac aagcttcacg aaggctccac | 60 |
| atacacagca gctgttcagt acaatgttct agaaaaagat gatgatcctg catcactaac | 120 |
| aatatgggtg cctatgttcc agtcatctgt accagcagac ttgctcataa agaacttgc | 180 |
| aagcatcaac atactagtga agcagatctc tacgcccaaa ggaccttcac tacgagtcac | 240 |
| gattaactca agaagtgctg tgctggctca aatgcctagt aatttcatca taagcgcaaa | 300 |
| tgtatcatta gatgaaagaa gcaaattagc atatgatgta actacacctt gtgaaatcaa | 360 |
| agcatgcagt ctaacatgct taaaagtgaa aagtatgtta actacagtca agatcttac | 420 |
| catgaagaca ttcaaccca ctcatgagat cattgctcta tgtgaatttg aaaatattat | 480 |
| gacatcaaaa agagtaataa taccaaccta tctaagacca attagtgtca aaacaagga | 540 |

```
tctgaactca ctagaaaaca tagcaaccac cgaattcaaa aatgctatca ccaatgcgaa    600
aattattccc tatgctggat tagtattagt tatcacagtt actgacaata aaggagcatt    660
caaatatatc aagccacaga gtcaatttat agtagatctt ggtgcctacc tagaaaaaga    720
gagcatatat tatgtgacta ctaattggaa gcatacagct acacgttttt caatcaaacc    780
actagaggat taaatttaat tatcaacact gaatgacagg tccacatata tcctcaaact    840
```

<210> SEQ ID NO 11
<211> LENGTH: 840
<212> TYPE: DNA
<213> ORGANISM: Human respiratory syncytial virus B

<400> SEQUENCE: 11

```
aaaagaacaa gatggggcaa atatggaaac atacgtgaac aagcttcacg aaggctccac     60
atacacagca gctgttcagt acaatgttct agaaaaagat gatgatcctg catcactaac    120
aatatgggtg cctatgttcc agtcatctgt accagcagac ttgctcataa agaacttgc    180 aagcatcaac atactagtga agcagatctc tacgcccaaa ggaccttcac tacgagtcac    240
gattaactca agaagtgctg tgctggctca aatgcctagt aatttcatca taagcgcaaa    300
tgtatcatta gatgaaagaa gcaaattagc atatgatgta actacacctt gtgaaatcaa    360
agcatgcagt ctaacatgct taaaagtgaa aagtatgtta actacagtca aagatcttac    420
catgaagaca ttcaaccccca ctcatgagat cattgctcta tgtgaatttg aaaatattat    480
gacatcaaaa agagtaataa taccaaccta tctaagacca attagtgtca aaaacaagga    540
tctgaactca ctagaaaaca tagcaaccac cgaattcaaa aatgctatca ccaatgcgaa    600
aattattccc tatgctggat tagtattagt tatcacagtt actgacaata aaggagcatt    660
caaatatatc aagccacaga gtcaatttat agtagatctt ggtgcctacc tagaaaaaga    720
gagcatatat tatgtgacta ctaattggaa gcatacagct acacgttttt caatcaaacc    780
actagaggat taaatttaat tatcaacact gaatgacagg tccacatata tcctcaaact    840
```

<210> SEQ ID NO 12
<211> LENGTH: 840
<212> TYPE: DNA
<213> ORGANISM: Human respiratory syncytial virus B

<400> SEQUENCE: 12

```
aaaagaacaa gatggggcaa atatggaaac atacgtgaac aagcttcacg aaggctccac     60
atacacagca gctgttcagt acaatgttct agaaaaagat gatgatcctg catcactaac    120
aatatgggtg cctatgttcc agtcatctgt accagcagac ttgctcataa agaacttgc    180 aagcatcaac atactagtga agcagatctc tacgcccaaa ggaccttcac tacgagtcac    240
gattaactca agaagtgctg tgctggctca aatgcctagt aatttcatca taagcgcaaa    300
tgtatcatta gatgaaagaa gcaaattagc atatgatgta actacacctt gtgaaatcaa    360
agcatgcagt ctaacatgct taaaagtgaa aagtatgtta actacagtca aagatcttac    420
catgaagaca ttcaaccccca ctcatgagat cattgctcta tgtgaatttg aaaatattat    480
gacatcaaaa agagtaataa taccaaccta tctaagacca attagtgtca aaaacaagga    540
tctgaactca ctagaaaaca tagcaaccac cgaattcaaa aatgctatca ccaatgcgaa    600
aattattccc tatgctggat tagtattagt tatcacagtt actgacaata aaggagcatt    660
caaatatatc aagccacaga gtcaatttat agtagatctt ggtgcctacc tagaaaaaga    720
gagcatatat tatgtgacta ctaattggaa gcatacagct acacgttttt caatcaaacc    780
```
actagaggat taaatttaat tatcaacact gaatgacagg tccacatata tcctcaaact     840

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gcattttgga caaagcgtct a                                              21

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tcacctctga ctaagggga                                                 19

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
agccgtgccc agtgagcggc t                                              21

<210> SEQ ID NO 16
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ccgtgcccag tgagcga                                                   17

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gctgaatttc ccatggagct c                                              21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cagaagagct gcaaagcaac a                                            21

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
aggggcaaag gatgtaatgg aagtgcccct                                   30

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ggcaaaggat gtaatggaag tgc                                          23

<210> SEQ ID NO 21
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tgcacttctt gagtttatca tgactctta                                    29

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cacgaaggct ccacatacac a                                            21

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
agggtgaaac aaatatccac accct                                        25

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gtgaaacaaa tatccacacc c                                            21

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
gcttgcaagt tcttttatga gcaa                                          24

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 26
cacgaaggct ccacatacac a                                             21

<210> SEQ ID NO 27
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
aggctgccta tgttccagtc atctgtacca gcagcct                            37

<210> SEQ ID NO 28
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 28
ctgcctatgt tccagtcatc tgtrccagca g                                  31

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 29
attcgccctt tgtttcgacc ta                                            22

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 30
ccgacgactg acgagcaa                                                 18

```
<210> SEQ ID NO 31
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tgcgaactgg caagct                                                    16

<210> SEQ ID NO 32
<211> LENGTH: 92
<212> TYPE: DNA
<213> ORGANISM: Influenza A virus

<400> SEQUENCE: 32
tcacctctga ctaaggggat tttrggrttt gtgttcacgc tcaccgtgcc cagtgagcgr     60
ggactgcarc gtagacgctt tgtccaaaat gc                                   92

<210> SEQ ID NO 33
<211> LENGTH: 121
<212> TYPE: DNA
<213> ORGANISM: Influenza B virus

<400> SEQUENCE: 33
cagaagagct gcaaagcaac attggagtat tgagatctct tggagcaagt caaaagaatg     60
gggaaggaat tgcaaaggat gtaatggaag tgctaaagca gagctccatg ggaaattcag    120
c                                                                    121

<210> SEQ ID NO 34
<211> LENGTH: 213
<212> TYPE: DNA
<213> ORGANISM: Human respiratory syncytial virus A

<400> SEQUENCE: 34
cacgaaggct ccacatacac agctgctgtt caatacaatg tcttagaaaa agacgatgac     60
cctgcatcac ttacaatatg ggtgcccatg ttccaatcat cyatgccagc agatttactt    120
ataaaagaac tagctaatgt caacatacta gtgaaacaaa tatccacacc caakggacct    180
tcaytaagag tcatgataaa ctcaagaagt gca                                 213

<210> SEQ ID NO 35
<211> LENGTH: 138
<212> TYPE: DNA
<213> ORGANISM: Human respiratory syncytial virus B

<400> SEQUENCE: 35
cacgaaggct ccacatacac agcagctgtt cagtacaatg ttctagaaaa agatgatgat     60
cctgcatcac taacaatatg ggtgcctatg ttccagtcat ctgtrccagc agacttgctc    120
ataaaagaac ttgcaagc                                                  138

<210> SEQ ID NO 36
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36
```

```
tgtgatggat atctgcagaa ttcgcccttt gtttcgacct agcttgccag ttcgcagaat    60
ttgttgctcg tcagtcgtcg gcggttttaa gggcgaattc cagcacactg gcggccgtta   120
```

<210> SEQ ID NO 37
<211> LENGTH: 323
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37

```
gcatgcgcat tttggacaaa gcgtctacgc tgcagtcccc gctcactggg cacggtgagc    60
gtgaacacaa atcctaaaat ccccttagtc agaggtgagg atcctgcact tcttgagttt   120
atcatgactc ttagtgaagg tcccttgggt gtggatattt gtttcactag tatgttgaca   180
ttagctagtt cttttataag taaatctgct ggcatagatg attggaacat gggcacccat   240
attgtaagtg atgcagggtc atcgtctttt tctaggacat tgtattgaac agcagctgtg   300
tatgtggagc cttcgtgggt acc                                           323
```

<210> SEQ ID NO 38
<211> LENGTH: 274
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38

```
gcatgcagag ctgaatttcc catagagctc tgttttagca cttccattac atctttggca    60
attccttctc cattctttg acttgctcct agagatctca acactccaat gttgctttgc    120
agctggatcc gcttgcaagt tcttttatga gcaagtctgc tggtacagat gactggaaca   180
taggcaccca tattgttagt gatgcaggat catcatcttt ttctagaaca ttgtactgaa   240
cagctgctgt gtatgtggag ccttcgtggg tacc                               274
```

<210> SEQ ID NO 39
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39

```
tgcgaactgg caagct                                                    16
```

<210> SEQ ID NO 40
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40

```
ccgtgcccag tgagcgg                                                   17
```